United States Patent [19]
Zahler et al.

[11] Patent Number: 5,340,816
[45] Date of Patent: Aug. 23, 1994

[54] HYDROXYMETHYL(METHYLENECYCLO-PENTYL) PURINES AND PYRIMIDINES

[75] Inventors: Robert Zahler, Pennington; William A. Slusarchyk, Skillman, both of N.J.

[73] Assignee: E. R. Squibb & Sons, Inc., Princeton, N.J.

[21] Appl. No.: 4,006

[22] Filed: Jan. 15, 1993

Related U.S. Application Data

[60] Division of Ser. No. 763,033, Sep. 20, 1991, which is a continuation-in-part of Ser. No. 599,568, Oct. 18, 1990, abandoned.

[51] Int. Cl.$^5$ .............. A61K 31/505; A61K 31/52; C07D 239/02; C07D 473/00
[52] U.S. Cl. .................. 514/269; 514/274; 514/262; 544/309; 544/311; 544/312; 544/313; 544/314; 544/317; 544/276
[58] Field of Search ............ 544/311, 312, 313, 314, 544/317, 309; 514/269, 274

[56] References Cited

U.S. PATENT DOCUMENTS

| | | | |
|---|---|---|---|
| 4,968,674 | 11/1990 | Taniyama et al. | 544/276 |
| 4,997,925 | 3/1991 | Jarvi et al. | 536/26 |
| 5,049,671 | 9/1991 | Daluge | 544/276 |
| 5,057,630 | 10/1991 | Lackey et al. | 544/276 |
| 5,063,233 | 11/1991 | Chen et al. | 544/276 |
| 5,064,961 | 11/1991 | Bisacchi et al. | 544/276 |

FOREIGN PATENT DOCUMENTS

| | | |
|---|---|---|
| 360018 | 3/1990 | European Pat. Off. |
| 365849 | 5/1990 | European Pat. Off. |
| 88/07049 | 1/1988 | PCT Int'l Appl. |
| 91/01318 | 2/1991 | PCT Int'l Appl. |

OTHER PUBLICATIONS

Yoshitomi, Abst. Japanese Patent Applic. 3258818A, Derwent 88-348780, Oct. 1988.
Yamasa Shoyu, Abst. Japanese Patent Applic. 3215694A, Derwent 88-295964, Sep. 1988.
Takenuki, "Design, Synthesis, and Antineoplastic . . . ", J. Med. Chem., vol. 31, 1063-64, 1988.
Usui et al., "Synthesis of 8,2'-Methano . . . ", Chem. Pharm. Bull., vol. 34, pp. 1518-1523 (1986).
Sano et al., "Synthesis of 6,2'-Methano . . . ", Chem. Pharm. Bull., vol. 33, pp. 3617-3622 (1984).
Ueda et al., "Synthesis of 2'-Deoxy-6,2'-Ethano . . . ", Nucleosides & Nucleotides, 4(3), pp. 401-409 (1985).
Usui et al., "Synthesis of 2'-Deoxy-8,2'-ethanoadenosine . . . ", Chem. Pharm. Bull., vol. 34, pp. 15-23 (1986).
Ueda et al., "Synthesis and Biological Activity . . . ", Nucleosides & Nucleotides, 8(546), pp. 743-752 (1989).
Madhavan et al., "Synthesis and Antiviral Evaluation . . . ", J. Med. Chem., vol. 31, pp. 1798-1804 (1988).
Samano et al., "Synthesis of 2'(and 3')-Methylene . . . ", Abstract 326, 200 ACS National Meeting, Aug. 26, 1990.
Herdewijn et al., "Synthesis and Antiviral Activity . . . ", J. Med. Chem., vol. 28, pp. 550-555 (1985).
Griengl et al., "5-(Haloalkyl)-2'-deoxyuridines . . . ", J. Med. Chem., vol. 28, pp. 1679-1684 (1985).

*Primary Examiner*—Cecilia Tsang
*Attorney, Agent, or Firm*—Stephen B. Davis

[57] ABSTRACT

Antiviral activity is exhibited by compounds having the formula

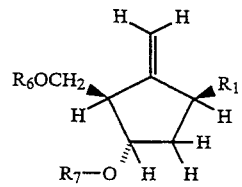

and its pharmaceutically acceptable salts.

20 Claims, No Drawings

HYDROXYMETHYL(METHYLENECYCLOPEN-TYL) PURINES AND PYRIMIDINES

RELATED APPLICATION

This application is a divisional of Ser. No. 763,033 filed Sep. 20, 1991 now U.S. Pat. No. 5,206,244, which is a continuation-in-part of Ser. No. 599,568 filed Oct. 18, 1990 now abandoned.

BRIEF DESCRIPTION OF THE INVENTION

Antiviral activity is exhibited by compounds having the formula

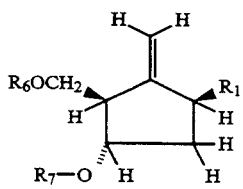

and its pharmaceutically acceptable salts. In formula I, and throughout the specification, the symbols are as defined below.

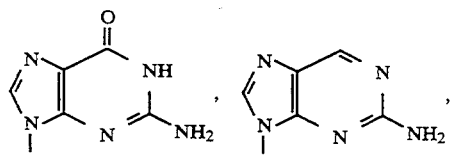

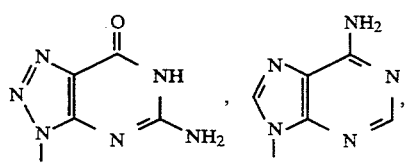

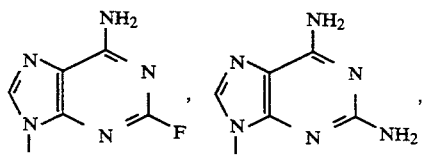

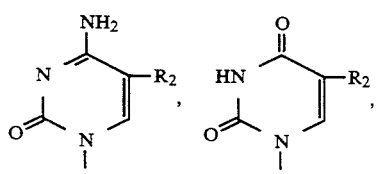

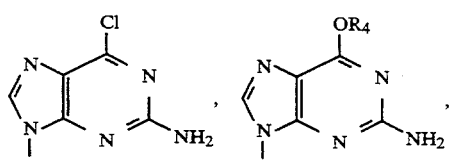

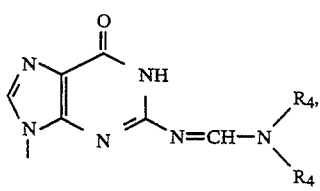

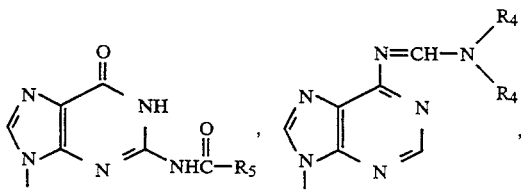

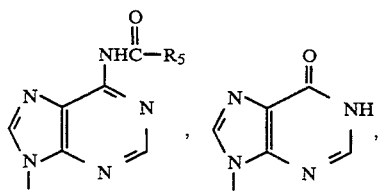

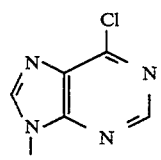

wherein $R_2$ is fluoro, chloro, bromo, iodo, hydrogen, methyl, trifluoromethyl, ethyl, n-propyl, 2-fluoroethyl, 2-chloroethyl, ethynyl, or

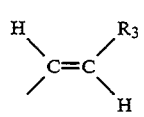

(trans)

wherein $R_3$ is chloro, bromo, iodo, hydrogen, methyl or trifluoromethyl; $R_4$ is alkyl; $R_5$ is hydrogen, alkyl, substituted alkyl, or aryl; and $R_6$ and $R_7$ are independently hydrogen, $-PO_3H_2$ or

Preferred compounds of formula 1 are when $R_1$ is

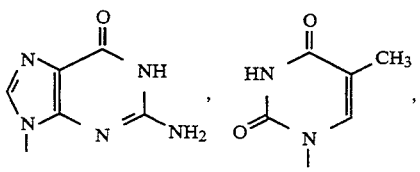

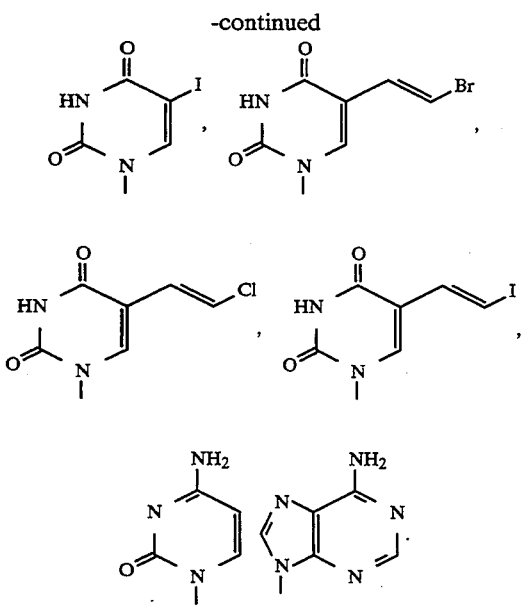

Most preferred compounds of formula 1 are when $R_1$ is

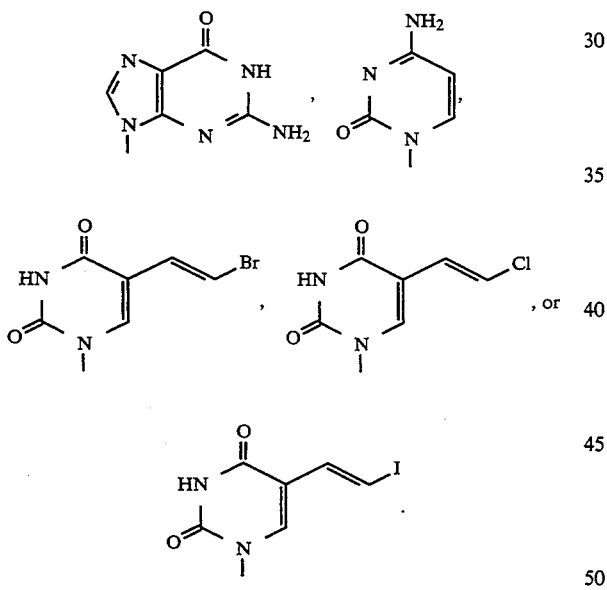

The term "alkyl" refers to both straight and branched chain groups. Those groups having 1 to 10 carbons are preferred. The term "substituted alkyl" refers to alkyl groups having one or more, preferably one, substituents. Preferred substituents are halogen, amino, azido, hydroxy, cyano, trialkylammonium (wherein each alkyl group has 1 to 6 carbons), alkoxy of 1 to 6 carbons, aryl and carboxy. The term "aryl" refers to phenyl and phenyl substituted with one, two or three substituents, preferably one. Preferred substitutents are alkyl of 1 to 6 carbons, alkoxy of 1 to 6 carbons, halogen, trifluoromethyl, amino, alkylamino of 1 to 6 carbons, dialkylamino, wherein each alkyl is of 1 to 6 carbons,nitro, cyano, alkanoyloxy of 2 to 11 carbons, carboxy, carbamoyl and hydroxy.

DETAILED DESCRIPTION OF THE INVENTION

The compounds of formula 1, and the pharmaceutically acceptable salts thereof, are antiviral agents that can be used to treat viral infection in mammalian species such as domesticated animals (e.g., dogs, cats, horses and the like) and humans, and avian species (e.g., chickens and turkeys). The compounds of formula 1 wherein $R_1$ is

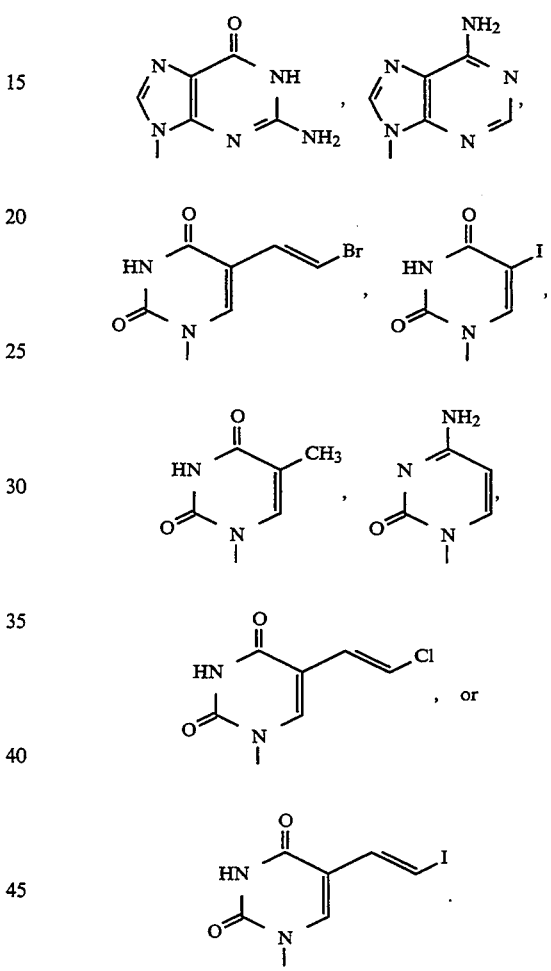

are effective against one or more of the following viruses: herpes simplex virus 1 and 2, varicella-zoster virus, and cytomegalovirus, They are also believed to be active against a variety of other DNA viruses. Exemplary DNA viruses in addition to those named above include other herpes viruses (e.g., Epstein-Barr virus, pseudorabies virus, human herpes virus 6, and the like), poxviruses (e.g. vaccinia virus, monkey pox, and myoma), papovaviruses (e.g., the papilloma viruses), hepatitis B virus, and adeno-viruses. All of the other compounds of formula 1 are believed to be active against one or more of the following viruses: herpes simplex virus 1 and 2, varicella-zoster virus, and cytomegalovirus The compounds of this invention may be administered parenterally (for example, by intravenous, intraperitoneal or intramuscular injection), orally or topically.

The compounds may be administered orally or parenterally in an amount effective to treat the infection. The dosage will, of course, depend on the severity of the infection, but will likely be in the range of about 1.0 to 50 mg/kg of body weight. The desired dose may be administered several times daily at appropriate intervals.

For infections of the eye, or other external tissues, (e.g. mouth and skin), the compositions may be applied to the infected part of the body of the patient topically as an ointment, cream, aerosol, gel, powder, lotion, suspension or solution (e.g. as in eye drops). The concentration of the compound in the vehicle will, of course, depend on the severity of the infection, but will likely be in the range of about 0.1 to 7% by weight.

The compounds of this invention can be prepared from a compound of formula

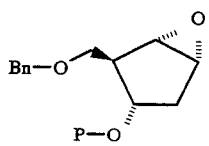   2 wherein "Bn" is

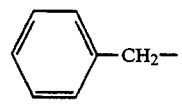

and P is a protecting group such as a benzyl, trityl, substituted trityl (e.g. 4-monomethoxytrityl or 4,4'-dimethoxytrityl), or silyl group. The term silyl refers to silyl protecting groups well known in the art [e.g. t-butyldimethylsilyl, t-butyldiphenylsilyl, (triphenylmethyl)dimethylsilyl, methyldiisopropylsilyl, or triisopropylsilyl]. Protection of the hydroxyl group in the known compound of formula

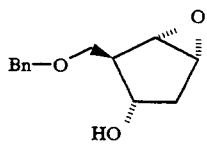   3 using benzyl bromide and sodium hydride affords the known compound of formula 2 wherein P is a benzyl group [see K. Biggadike et. al, *J. Chem. Soc. Perkin Trans,* 1 549 (1988)]. Protection with a trityl, substituted trityl or silyl group can be accomplished by methods known in the art.

A compound of formula 1 wherein $R_1$ is

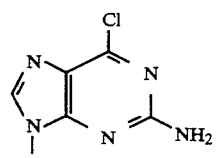

and $R_6$ and $R_7$ are hydrogen can be prepared by reaction of a compound of formula 2 with a compound of formula

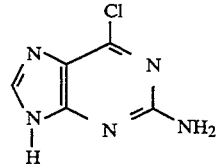   4 in the presence of a base such as lithium hydride, sodium hydride, or potassium hydride in an aprotic polar solvent such as dimethylformamide, dimethyl sulfoxide, or sulfolane (tetramethylene sulfone). This yields the corresponding compound of formula

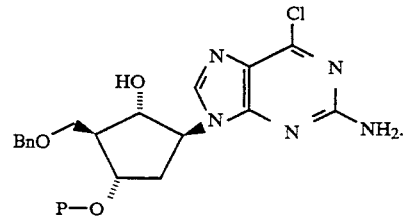   5

Protection of the amino (—$NH_2$) group in the compound of formula 5 affords a compound of formula

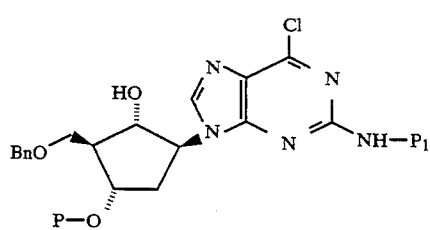   6 wherein the protecting group $P_1$ can be trityl or substituted trityl (e.g. 4-monomethoxytrityl or 4,4'-dimethoxytrityl). The protection can be accomplished by treatment of the compound of formula 5 with trityl chloride or a substituted trityl chloride in dichloromethane in the presence of triethylamine (and, optionally, in the presence of 4-N,N-dimethylaminopyridine). Oxidation of the hydroxyl group in this compound of formula 6 yields a compound of formula

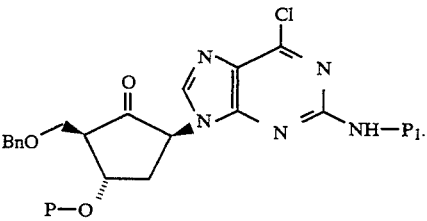   7

The oxidation can be carried out by methods well know in the art (e.g. 1,3-dicyclohexylcarbodiimide/-dimethyl sulfoxide/methylphosphonic acid in dichloromethane or pyridinium dichromate/molecular sieves in dichloromethane). Treatment of a compound of formula 7 with a methylenation reagent such as zinc-/titanium tetrachloride/dibromomethane in dichloromethane/tetrahydrofuran or methylenetriphenylphosphorane yields a compound of formula

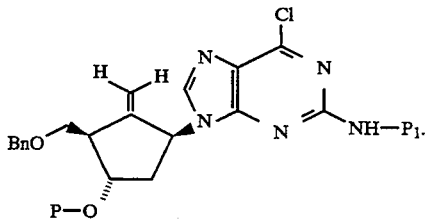

Removal of the protecting groups from a compound of formula 8 provides the compound of formula 1 wherein $R_1$ is

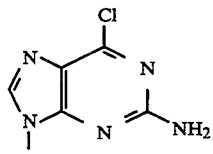

and $R_6$ and $R_7$ are hydrogen. When the protecting groups P and $P_1$ are trityl or substituted trityl, removal of the trityl groups P and $P_1$ can be accomplished by treatment with aqueous alcoholic mineral acid (e.g. hydrochloric acid in aqueous methanol) or aqueous acetic acid. Subsequently, the benzyl group protecting the primary hydroxyl group can be removed by treatment with boron trichloride in dichloromethane. When the protecting group P is benzyl and the $P_1$ protecting group is trityl or substituted trityl, the $P_1$ protecting group can be removed by treatment with aqueous alcoholic mineral acid or aqueous acetic acid, and the benzyl protecting groups can be removed with boron trichloride. When the protecting group P is a silyl group and $P_1$ is a trityl or substituted trityl group, the silyl group can be removed first by treatment with fluoride ion (e.g. tetrabutylammonium fluoride in tetrahydrofuran). Subsequently, the $P_1$ protecting group can be removed by treatment with aqueous alcoholic mineral acid or aqueous acetic acid, and then the benzyl group protecting the primary alcohol group can be removed by treatment with boron trichloride. Alternatively, the $P_1$ protecting group can be removed first, the silyl protecting group P second, and the benzyl group protecting the primary alcohol last.

The compound of formula 1 wherein $R_1$ is

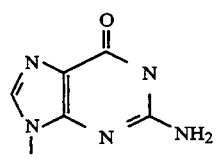

and $R_6$ and $R_7$ are hydrogen can be prepared as follows:

Reaction of a compound of formula 2 with a compound of formula

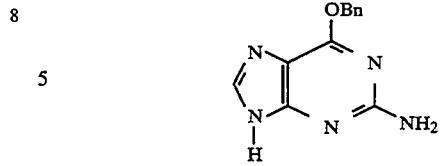

according to procedures analogous to those used in preparation of the compound of formula 5 affords a compound of formula

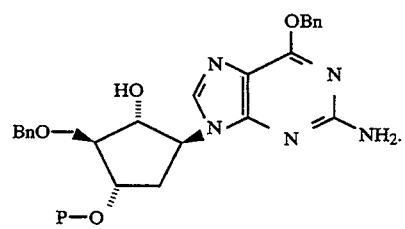

Protection of the amino group (—$NH_2$) in the compound of formula 10 according to the procedures analogous to those used in the preparation of the compound of formula 6 yields a compound of formula

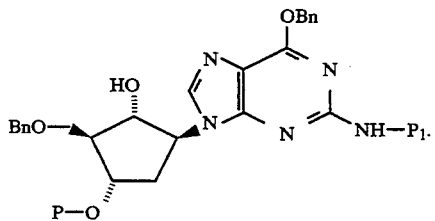

Oxidation of the alcohol group in the compound of formula 11 under conditions analogous to those used in the preparation of the compound of formula 7 provides a compound of formula

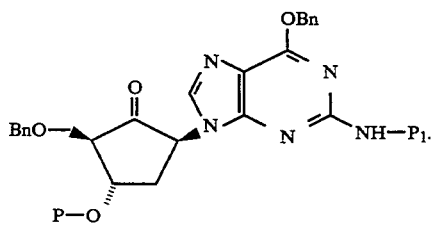

Methylenation of the ketone group in the compound of formula 12 under conditions analogous to those used in the preparation of the compound of formula 8 yields a compound of formula

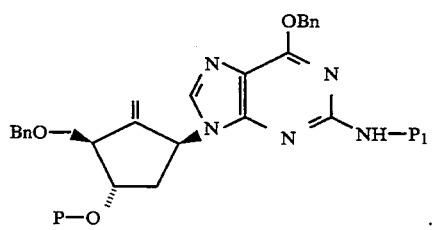

Finally, removal of the protecting groups from the compound of formula 13 provides the compound of formula 1 wherein R₁ is

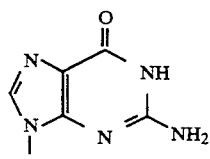

and R₆ and R₇ are hydrogen. When the protecting groups P and P₁ are trityl or substituted trityl, removal of the trityl groups and the purine O-benzyl protecting group can be accomplished by treatment with aqueous alcoholic mineral acid (e.g. hydrochloric acid in aqueous methanol). Subsequently, the benzyl group protecting the primary hydroxyl can be removed by treatment with boron trichloride in dichloromethane. When the protecting group P is benzyl and the P₁ protecting group is trityl or substituted trityl, the P₁ protecting group and the purine O-benzyl protecting group can be removed first by treatment with aqueous alcoholic mineral acid. Subsequently, the benzyl groups protecting the alcohol groups can be removed by treatment with boron trichloride. When the protecting group P is a silyl group and P₁ is a trityl or substituted trityl group, the silyl group can be removed first by treatment with fluoride ion (e.g. tetrabutylammonium fluoride in tetrahydrofuran). Subsequently, the P₁ protecting group and the purine O-benzyl protecting group can be removed by treatment with aqueous alcoholic mineral acid. Finally, the benzyl group protecting the primary alcohol can be removed by treatment with boron trichloride. Alternatively, the P₁ and purine O-benzyl protecting groups can be removed first, the silyl protecting group P second, and the benzyl group protecting the primary alcohol last.

Alternatively, this compound can be prepared from a compound of formula 1 wherein R₁ is

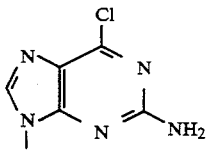

and R₆ and R₇ are hydrogen, by hydrolysis of the chloro group using aqueous acid (e.g. aqueous hydrochloric acid).

The compound of formula 1 wherein R₁ is

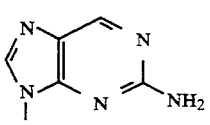

and R₆ and R₇ are hydrogen can be prepared from the compound of formula 5 wherein P is a silyl group (e.g. t-butyldiphenylsilyl). Hydrogenolysis of this compound (e.g. ammonium formate and palladium on carbon in methanol; palladium hydroxide on carbon and cyclohexene in ethanol; or palladium on carbon, hydrogen, and ethanol) results in reduction of the chloro group and removal of the benzyl protecting group on the primary hydroxyl to afford the compound of formula

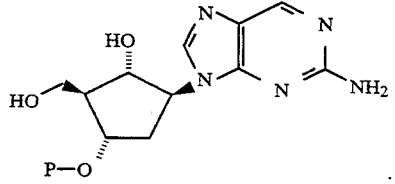

Protection of the primary hydroxyl group and the amino (—NH₂) group in the compound of formula 14 by reaction with trityl chloride or a substituted trityl chloride in dichloromethane in the presence of triethylamine and 4-N,N-dimethylaminopyridine affords the compound of formula

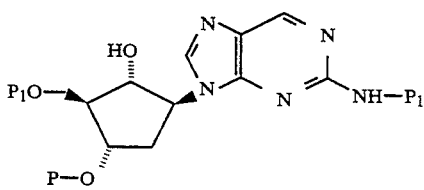

where the P₁ groups are trityl or substituted trityl. Sequential oxidation and methylenation of the compound of formula 15 under conditions analogous to those used in the preparation of the compounds of formulas 7 and 8, respectively, followed by removal of the protecting groups, affords the compound of formula 1 wherein R₁ is

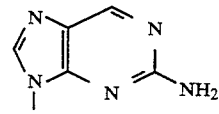

and R₆ and R₇ are hydrogen. The silyl protecting group P can be removed first by treatment with fluoride ion (e.g. tetrabutylammonium fluoride in tetrahydrofuran), and then the trityl protecting groups P₁ can be removed by treatment with aqueous alcoholic mineral acid (e.g. hydrochloride acid in aqueous methanol) or aqueous acetic acid. Alternatively, the trityl protecting groups P₁ can be removed first followed by removal of the silyl protecting group P.

Alternatively, reaction of the compound of formula

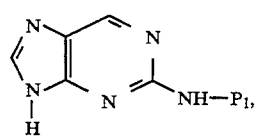

wherein P₁ is a trityl or substituted trityl group, with a compound of formula 2 under conditions analogous to those used in the preparation of the compound of formula 5 affords a compound of formula

17

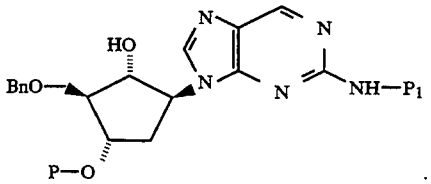

Sequential oxidation and methylenation of the compound of formula 17 under conditions analogous to those used in the preparation of the compounds 7 and 8, respectively, followed by removal of the protecting groups affords the compound of formula 1 wherein $R_1$ is

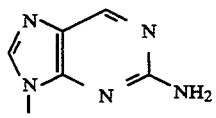

and $R_6$ and $R_7$ are hydrogen.

Alternatively, reaction of a compound of formula

18

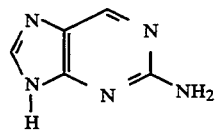

with a compound of formula 2 affords a compound of formula

19

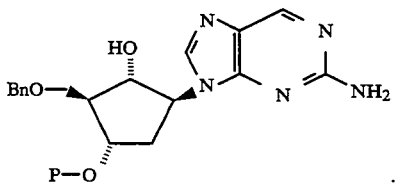

Protection of the amino (—$NH_2$) group with a trityl or substituted trityl group provides the compound of formula 17, which can then be converted (as described above) to the compound of formula 1 wherein $R_1$ is

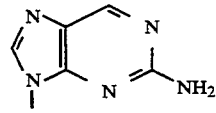

and $R_6$ and $R_7$ are hydrogen.

The compound of formula 1 wherein $R_1$ is

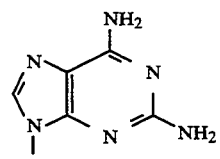

and $R_6$ and $R_7$ are hydrogen can be prepared from a compound of formula 8 by methods known in the art. Thus, for example, when a compound of formula 8 (wherein P is a protecting group such as benzyl, silyl, trityl or substituted trityl, and $P_1$ is trityl or substituted trityl) is treated with hot methanolic ammonia, displacement of the chloro group with an amino group will result. The protecting groups can then be removed according to procedures known in the art.

Alternatively, this compound of formula 1 can be prepared from a compound of formula 1 wherein $R_1$ is

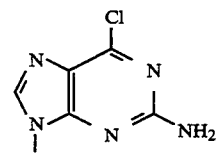

and $R_6$ and $R_7$ are hydrogen by methods known in the art. (See, e.g., J. C. Martin, et al, *J. Med. Chem.* 28, 358 (1985)).

A compound of formula 1 wherein $R_1$ is

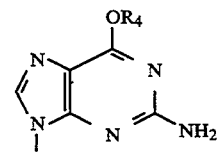

and $R_6$ and $R_7$ are hydrogen can be prepared by treatment of a compound of formula 5 with sodium alkoxide, which provides the compound of formula

20

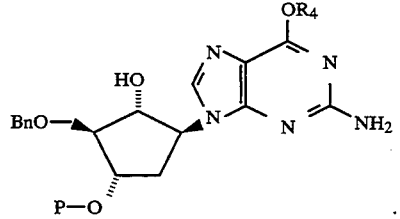

Protection of the amino group, oxidation and methylenation (according to procedures analogous to those used in the preparation of compounds 6, 7 and 8), followed by removal of protecting groups, provides the compound of formula 1 wherein $R_1$ is

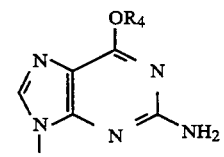

and $R_6$ and $R_7$ are hydrogen.

Alternatively, this compound of formula 1 can be prepared from a compound of formula 1 wherein $R_1$ is

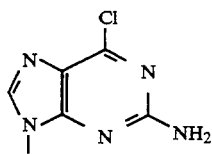

and R₆ and R₇ are hydrogen by methods known in the art. See, for example, J. F. Gerster, et al., *J. Amer. Chem. Soc.*, 87, 3752 (1965); K. K. Ogilvie, et al., *Can. J. Chem.*, 62, 2702 (1984); M. R. Harnden, et al., *J. Med. Chem.*, 30, 1636 (1987).

Alternatively, this compound of formula 1 can be prepared from a compound of formula

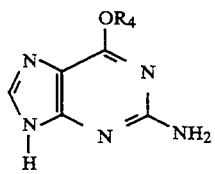

and a compound of formula 2 using procedures analogous to those used in the preparation of compounds 5, 6, 7 and 8, followed by removal of the protecting groups. A compound of formula 21 can be prepared from the compound of formula 21 by methods know in the art (See, e.g., W. A. Bowles, et al., *J. Med. Chem.*, 6, 471 (1963); M. MacCoss, et al., *Tetrahedron Lett.*, 26, 1815 (1985)).

The compound of formula 1 wherein R₁ is

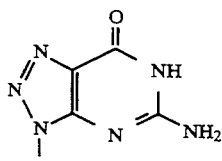

and R₆ and R₇ are hydrogen can be prepared from a compound of formula 2 and a compound of formula

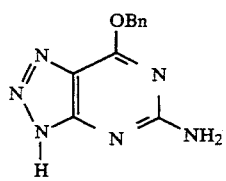

according to procedures analogous to those used in preparation of compounds 10, 11, 12, and 13, followed by removal of the protecting groups.

The compound of formula 1 wherein R₁ is

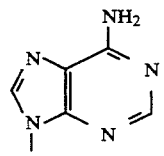

and R₆ and R₇ are hydrogen can be prepared as follows: Reaction of the compound of formula

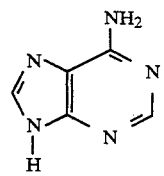

with a compound of formula 2 according to procedures analogous to those used in preparation of the compound of formula 5, affords a compound of formula

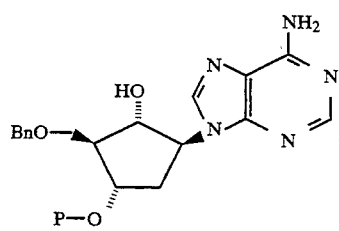

Selective protection of the amino (—NH₂) group in the compound of formula 24 with an acyl group P₂ (e.g., acetyl) gives the compound of formula

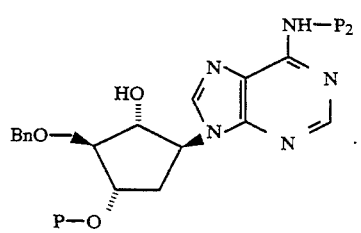

See, for example, G. S. Ti et al., *J. Amer. Chem. Soc.*, 104, 1316 (1982)). Oxidation of the compound of formula 25 and subsequent treatment with zinc/titanium tetrachloride/dibromomethane according to procedures analogous to those used in the preparation of compounds 7 and 8 provides a compound of formula

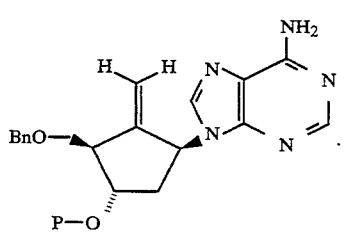

Removal of the protecting groups from this compound yields the compound of formula 1 wherein R₁ is

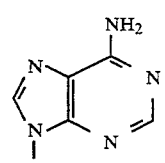

and R₆ and R₇ are hydrogen.

Alternatively, oxidation of the compound of formula 25 and subsequent treatment with methylenetriphenylphosphorane according to procedures analogous to those used for the preparation of compounds 7 and 8 gives the compound of formula 26 wherein the amino (—NH$_2$) group still possesses an acyl protecting group, P$_2$. Removal of the protecting groups from this compound provides the compound of formula 1 wherein R$_1$ is

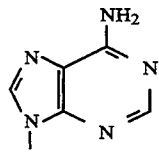

and R$_6$ and R$_7$ are hydrogen. (Removal of the acyl protecting group P$_2$ can be accomplished using sodium methoxide in methanol or methanolic ammonia).

Alternatively, this compound of formula 1 can be prepared by reaction of the compound of formula

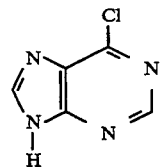

27 with a compound of formula 2 under conditions analogous to those used for the preparation of the compound of formula 5. Subsequent oxidation and methylenation according to procedures analogous to those used in the preparation of compounds 7 and 8 provides the compound of formula

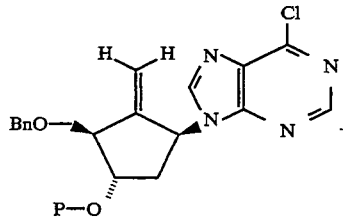

28

Treatment of a compound of formula 28 with hot ammonia in an alcohol (such as methanol or ethanol) followed by removal of protecting groups yields the compound of formula 1 wherein R$_1$ is

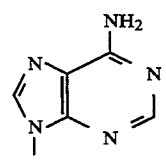

and R$_6$ and R$_7$ are hydrogen.

In another alternative, this compound of formula 1 can be prepared from a compound of formula 1 wherein R$_1$ is

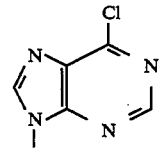

and R$_6$ and R$_7$ are hydrogen by methods known in the art. (See e.g. J. C. Martin et al., *J. Med. Chem.*, 28, 358 (1985)).

The compound of formula 1 wherein R$_1$ is

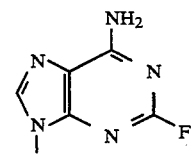

and R$_6$ and R$_7$ are hydrogen can be prepared by removal of the protecting groups from the compound of formula 28.

The compound of formula 1 wherein R$_1$ is

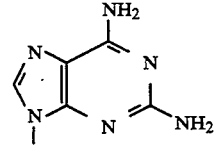

and R$_6$ and R$_7$ are hydrogen can be prepared from the compound of formula 1 wherein R$_1$ is

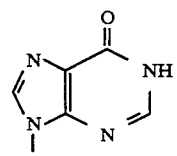

and R$_6$ and R$_7$ are hydrogen by following known procedures. See, for example, J. A. Montgomery et al., "Synthetic Procedures in Nucleic Acid Chemist", Vol. 1, W. W. Zorbach and R. S. Tipson, Eds., Interscience Publishers (John Wiley and Sons), N. Y. p. 205, 1968.

The compound of formula 1 wherein R$_1$ is and R$_6$ and R$_7$ are hydrogen can be prepared from this compound of formula 1 wherein R$_1$ is

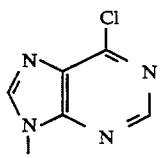

and R$_6$ and R$_7$ are hydrogen by acid hydrolysis (e.g. hot aqueous hydrochloric acid) or basic hydrolysis (e.g., aqueous methanolic sodium hydroxide).

Alternatively, this compound of formula 1 can be prepared by treatment of a compound of formula 1 wherein R$_1$ is

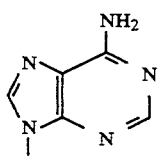

and R$_6$ and R$_7$ are hydrogen with adenosine deaminase or nitrous acid according to methods known in the art (e.g., M. J. Robins, et al., *J. Med. Chem.*, 27, 1486 (1984); K. K. Ogilvie et al, *Can. J. Chem.*, 62 241 (1984)); I. Iwai, et al., in "Synthetic Procedures in Nucleic Acid Chemistry", Vol. 1, W. W. Zorbach and R. S. Tipson, Eds., Interscience Publishers (John Wiley and Sons), N. Y., p. 135, 1968; R. E. Holmes et al., *J. Amer. Chem. Soc.*, 86, 1242 (1964)).

The compound of formula

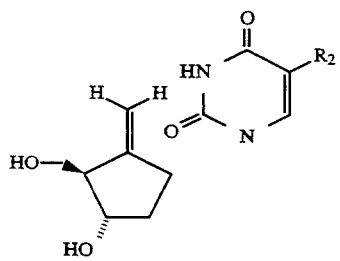

wherein R$_2$ is hydrogen, fluoro, methyl, ethyl, n-propyl, 2-chloroethyl, or 2-fluoroethyl can be prepared by reaction of the corresponding compound of formula

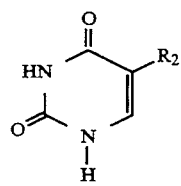

with a compound of formula 2 in the presence of a base such as lithium hydride, sodium hydride, or potassium hydride in an aprotic polar solvent such as dimethylformamide, dimethyl sulfoxide or sulfolane to yield a compound of formula

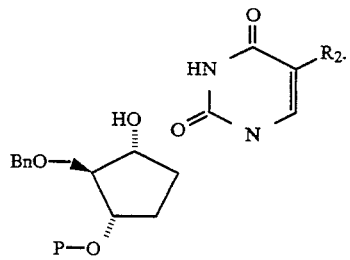

Oxidation of the hydroxyl group in a compound of formula 31 using methods known in the art (e.g. 1,3-dicyclohexylcarbodiimide/dimethylsulfoxide/methylphoshonic acid in dichloromethane or pyridinium dichromate/molecular sieves in dichloromethane) provides the compound of formula

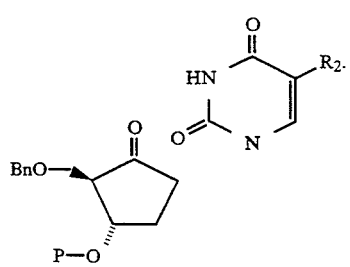

Treatment of the compound of formula 32 with a methylenation reagent such as zinc/titanium tetrachloride/dibromomethane in dichloromethane/tetrahydrofuran or methylenetriphenylphosphorane yields the compound of formula

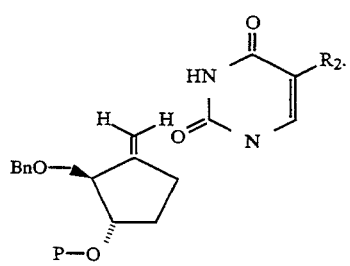

Removal of the protecting groups from the compound of formula 33 provides the corresponding compound of formula 29. For example, when the protecting group P is benzyl, both benzyl groups can be removed by treatment with boron trichloride in dichloromethane. When the protecting group P is trityl or substituted trityl, the trityl protecting group can be removed by treatment with aqueous acetic acid or aqueous alcoholic mineral acid, (e.g., hydrochloric acid in aqueous methanol), and then the benzyl protecting group can be removed by treatment with boron trichloride. When the protecting group P is a silyl group, removal of the silyl protecting group can be accomplished with fluoride ion (e.g. tetrabutylammonium fluoride in tetrahydrofuran) and then the benzyl group can be removed by treatment with boron trichloride. Alternatively, the benzyl group can be removed first, followed by removal of the silyl group.

The compound of formula 30 wherein R$_2$ is 2-chloroethyl or 2-fluoroethyl can be prepared by methods known in the art (H. Griengl et. al., *J. Med.*, 30 1199 (1987); *J. Med. Chem.*, 28 1679 (1985)).

The compound of formula 31 wherein $R_6$ is fluoro can also be prepared from the corresponding compound 31 wherein $R_2$ is hydrogen and the protecting group P is benzyl, trityl or substituted trityl by fluorination using trifluoromethyl hypofluorite following methodology known in the art. For example, see M. J. Robins, et al., *J. Amer. Chem. Soc.*, 93 5277 (1971); *Chem. Communs.*, 18 (1972); T. S. Lin et al., *J. Med. Chem.*, 26, 1691 (1983).

The compounds of formula 29 wherein $R_2$ is 2-chloroethyl and 2-fluoroethyl can also be prepared from a compound of formula

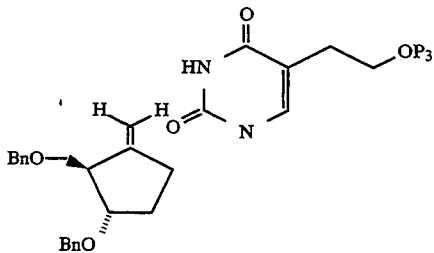

34 wherein $P_3$ is trityl, substituted trityl, or a silyl protecting group. Removal of the $P_3$ protecting group yields a compound of formula 33 wherein P is benzyl and $R_2$ is 2-hydroxyethyl. Treatment of this compound with triphenylphosphinecarbon tetrachloride, and subsequent removal of the benzyl protecting groups with boron trichloride, affords the compound of formula 29 wherein $R_2$ is 2-chloroethyl. Similar treatment using triphenylphosphine/N-bromosuccinimide or triphenylphosphine/N-bromosuccinamide/tetrabutylammonium iodide in place of triphenylphosphine/carbon tetrachloride (e.g., see H. Griengl, et al., *J. Med. Chem.*, 28, 1679 (1985)) affords compounds of formula 33 wherein P is benzyl and $R_2$ is 2-bromoethyl or 2-iodoethyl, respectively. Subsequent treatment with fluoride ion, followed by removal of the benzyl protecting groups, provides the compound of formula 29 wherein $R_2$ is 2-fluoroethyl. Alternatively, treatment of a compound of formula 33 wherein P is benzyl and $R_2$ is 2-hydroxyethyl with diethylaminosulfur trifluoride provides, upon removal of the benzyl protecting groups, a compound of formula 29 wherein $R_2$ is 2-fluoroethyl.

The compound of formula 34 can be prepared from a compound of formula

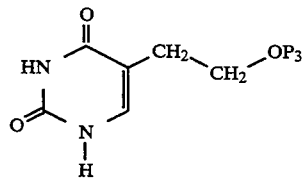

35 and a compound of formula 2 by methods analogous to those used in the preparation of compounds 31, 32 and 33 wherein $R_2$, for example, is hydrogen, methyl or ethyl, and P is benzyl. The compound of formula 35 can be prepared from the corresponding free alcohol by methods known in the art.

The compound of formula

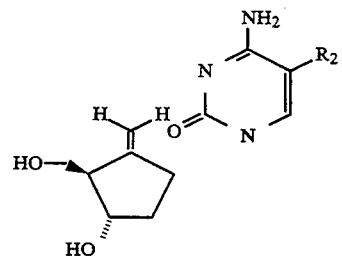

36 wherein $R_2$ is hydrogen, fluoro, methyl, ethyl, n-propyl, 2-chloroethyl or 2-fluoroethyl can be prepared from the corresponding compound of formula 33 wherein the protecting group P is a benzyl, trityl, substituted trityl or silyl group. Treatment of this compound with, for example, 4-chlorophenyl dichlorophosphate and 1,2,4-triazole in a solvent such as pyridine and reaction of the resulting intermediate with ammonium hydroxide in a solvent such as dioxane provides the corresponding compound of formula

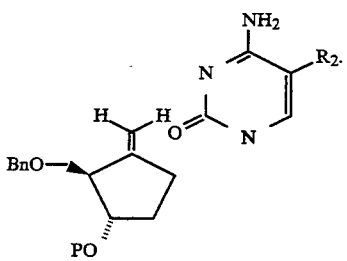

37

See, for example, T. S. Lin et al., *J. Med. Chem.*, 26, 1691 (1983); P. Herdewijn, et al., *J. Med. Chem.*, 28, 550 (1985). Removal of the protecting groups from the compound of formula 37 yields the corresponding compound of formula 36. For example, if P is a benzyl group, both benzyl protecting groups can be removed by treatment with boron trichloride. If P is a trityl or substituted trityl protecting group, the P group can be removed with aqueous alcoholic mineral acid or aqueous acetic acid, and the benzyl group protecting the primary alcohol can be removed with boron trichloride. If P is a silyl protecting group, the P group can be removed with fluoride ion followed by removal of the benzyl protecting group. Alternatively, the benzyl protecting group can be removed with boron trichloride followed by removal of the silyl protecting group with fluoride ion.

Alternatively, the compound of formula 33 wherein $R_2$ is hydrogen, fluoro, methyl, ethyl, n-propyl, 2-chloroethyl or 2-fluoroethyl and the protecting group P is a benzyl, trityl, substituted trityl or silyl group can be reacted with a sulfonyl chloride (e.g., p-toluenesulfonyl chloride) in an inert solvent (e.g., 1,2-dichloroethane or dioxane) in the presence of a base such as potassium carbonate. (For other sulfonyl chlorides and solvents, see, for example, European Patent Application EP 204, 264 ). This affords the corresponding compound of formula

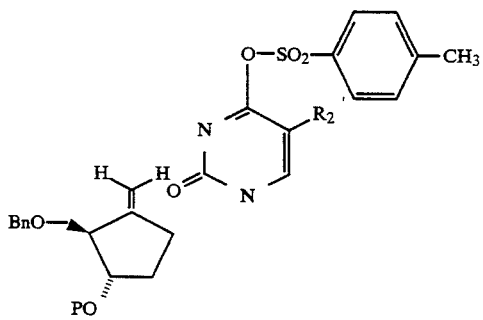

which can be treated with ammonia gas in an inert solvent (e.g., 1,2-dichloroethane or dioxane) to afford the corresponding compound of formula 37. Removal of the protecting groups from the compound of formula 37 yields the corresponding compound of formula 36.

Alternatively, the compound of formula 3.6 wherein $R_2$ is fluoro, hydrogen, methyl, ethyl, n-propyl, 2-chloroethyl or 2-fluoroethyl can be prepared from the corresponding compound of formula 29 by methods known in the art. See, for example, T. S. Lin, et al., *J. Med. Chem.*, 26, 1691 (1983); P. Herdewijn, et al., *J. Med. Chem.*, 28, 550 (1985); European Patent Application EP 360018.

Alternatively, the compound of formula 36 wherein $R_2$ is fluoro, hydrogen, methyl, ethyl, n-propyl, 2-chloroethyl or 2-fluoroethyl can be prepared by reaction of the corresponding compound of formula

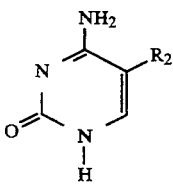

with a compound of formula 2 in the presence of a lithium hydride, sodium hydride or potassium hydride in an aprotic polar solvent such as dimethylformamide, dimethyl sulfoxide or sulfolane to yield a compound of formula

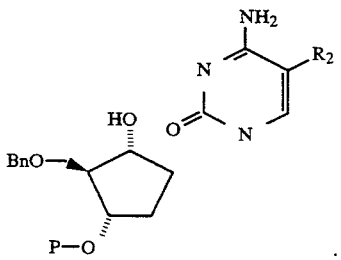

Selective protection of the amino group in the compound of formula 40 with an acyl group $P_2$ (e.g. acetyl) yields a compound of formula

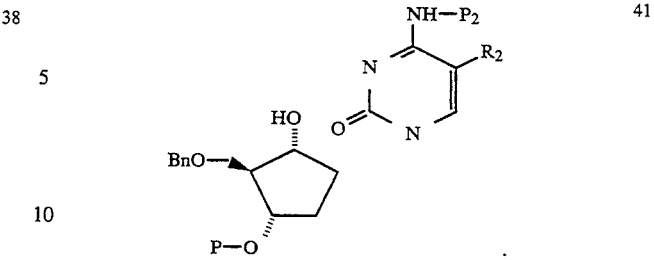

(See, for example, G. S. Ti et al., *J. Amer. Chem. Soc.*, 104, 1316 (1982)). Oxidation of the compound of formula 41, followed by methylenation with zinc/titanium tetrachloride/dibromomethane, with subsequent or simultaneous removal of the acyl protecting group $P_2$, gives a compound of formula 37. Removal of the protecting groups from this compound provides a compound of formula 36 wherein $R_2$ is fluoro, hydrogen, methyl, ethyl, n-propyl, 2-chloroethyl or 2-fluoroethyl. When the protecting group P is benzyl, both benzyl groups can be removed by treatment with boron trichloride in dichloromethane. When the protecting group P is trityl or substituted trityl, the trityl protecting group can be removed by treatment with aqueous acetic acid or aqueous alcoholic mineral acid (e.g., hydrochloric acid in aqueous methanol), and then the benzyl protecting group can be removed by treatment with boron trichloride. When the protecting group P is a silyl group, removal of the silyl protecting group can be accomplished with fluoride ion (e.g., tetrabutylammonium fluoride in tetrahydrofuran) and then the benzyl group can be removed by treatment with boron trichloride. Alternatively, the benzyl group can be removed first followed by removal of the silyl group.

Alternatively, oxidation of the compound of formula 41 and subsequent treatment with methylenetriphenylphosphorane gives a compound of formula

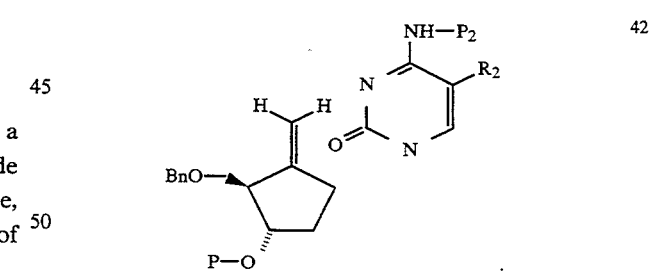

Removal of the protecting groups from this compound provides the compound of formula 36 wherein $R_2$ is fluoro, hydrogen, methyl, ethyl, n-propyl, 2-chloroethyl or 2-fluroethyl. Removal of the acyl protecting group $P_2$ can be accomplished using sodium methoxide in methanol or methanolic ammonia.

Alternatively, the compound of formula 40 wherein $R_2$ is hydrogen, fluoro, methyl, ethyl, n-propyl, 2-chloroethyl or 2-fluoroethyl and the protecting group P is a benzyl, trityl, or silyl group can be prepared from the corresponding compound of formula 31 using methodology known in the art. See, for example, T. S. Lin et al., *J. Med. Chem.*, 26, 1691 (1983); P. Herdewijn et al., *J. Med. Chem.*, 28, 550 (1985); European Patent Applications EP 360018 and EP 204264.

Alternatively, the compound of formula 40 or 41 wherein $R_2$ is fluoro can be prepared from the corresponding compound of formula 40 or 41 wherein $R_2$ is hydrogen and the protecting group P is benzyl, trityl or substituted trityl by fluorination using trifluoromethyl hypofluorite following methodology known in the art. For example, see M. J. Robins, et al., *J. Amer. Chem. Soc.*, 93, 5277 (1971) and *Chem. Communs.*, 18 (1972); T. S. Lin et al., *J. Med. Chem.*, 26, 1691 (1983).

The compound of formula 29 wherein $R_2$ is chloro, bromo or iodo can be prepared from the compound of formula 31 wherein $R_2$ is hydrogen and the protecting group P is a benzyl group. Halogenation of this compound of formula 31 by methods known in the art provides the corresponding compound of formula

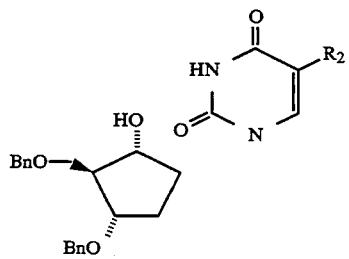

wherein $R_2$ is chloro, bromo or iodo. (See, for example, P. Herdewijn et al., *J. Med. Chem.*, 28, 550 (1985); M. J. Robins et .al., *J. Org. Chem.*, 48, 1854 (1983); T. S. Lin et al., *J. Med. Chem.*, 26, 598 (1983); T. Ueda et al., *Nucleotides and Nucleosides*, 4, 401 (1985); "Synthetic Procedures in Nucleic Acid Chemistry", Vol. 1, W. W. Zorback and R. S. Tipson, Eds., John Wiley and Sons, NY, p. 491, 1968). Oxidation of the compound of formula 43 and subsequent methylenation with zinc/titanium tetrachloride/dibromomethane or methylenetriphenylphosphorane provides the compound of formula

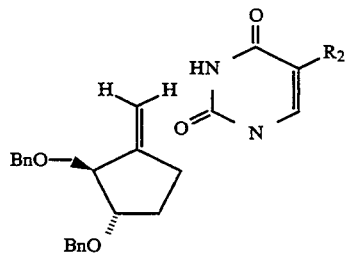

wherein $R_2$ is chloro, bromo or iodo. (See, for example, European Patent Application EP 360018). Removal of the benzyl protecting groups in the compound of formula 44 by treatment with boron trichloride affords the compound of formula 29 wherein $R_2$ is chloro, bromo, or iodo.

The compound of formula 36 wherein $R_2$ is chloro, bromo or iodo can be prepared from the corresponding compound of formula 44 using methods known in the art (and analogous to those used in the conversion of compound 33 to compound 37 wherein, for example, $R_2$ is hydrogen, methyl or ethyl), followed by removal of the benzyl protecting groups with boron trichloride.

Alternatively, the compound of formula 36 wherein $R_2$ is chloro, bromo or iodo can be prepared from the corresponding compound of formula 29 by methods known in the art. See, for example, T. S. Lin, et al., *J. Med. Chem.*, 26, 1691 (1983); P. Herdewijn, et al., *J. Med. Chem.*, 28, 550 (1985); European Patent Applications EP 360018 and EP 204264).

The compound of formula 29 wherein $R_2$ is trifluoromethyl can be prepared from the compound of formula 44 wherein $R_2$ is iodo by treatment with trifluoromethyl iodide and copper followed by the removal of the benzyl protecting groups using boron trichloride. See, for example, Y. Kobayashi et al., *J. Chem. Soc. Perkin* 1, 2755 (1980); S. Lin et al., *J. Med. Chem.*, 26, 1691 (1983).

The compound of formula 29 wherein $R_2$ is trifluoromethyl can be prepared from a compound of formula 43 wherein $R_2$ is iodo as follows: A compound of formula 43 wherein $R_2$ is iodo can be converted to a compound of formula

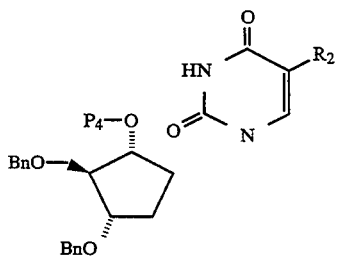

wherein $R_2$ is iodo and the protecting group $P_4$ is trityl, substituted trityl or acyl ( e.g., acetyl ). Treatment of this compound of formula 45 with trifluoromethyl iodide and copper according to procedures known in the art (see for example, Y. Kobayashi, et al., *J. Chem. Soc. Perkin*, 2755 (1980); S. Lin, et. al.; *J. Med. Chem.*, 26 1691 (1983)) and subsequent removal of the $P_4$ protecting group provides the compound of formula 43 wherein $R_2$ is trifluoromethyl. Oxidation of the compound of formula 43 wherein $R_2$ is trifluoromethyl and subsequent treatment with zinc/titanium tetrachloride/dibromomethane or methylenetriphenylphosphorane provides the compound of formula 44 wherein $R_2$ is trifluoromethyl. Removal of the benzyl protecting groups from the compound of formula 44 by treatment with boron trichloride provides the compound of formula 29 wherein $R_2$ is trifluoromethyl.

The compound of formula 36 wherein $R_2$ is trifluoromethyl can be prepared from the corresponding compound of formula 44 using methods known in the art (and analogous to those used in the conversion of compound 33 to compound 37 wherein, for example, $R_2$ is hydrogen, methyl, or ethyl ), followed by removal of the benzyl protecting groups with boron trichloride.

Alternatively, the compound of formula 36 wherein $R_2$ is trifluoromethyl can be prepared from the corresponding compound of formula 29 by methods known in the art. See, for example, T. S. Lin et al., *J. Med. Chem.*, 26, 1691 (1983); P. Herdewijn et al., *J. Med. Chem.*, 28, 550; (1985); European Patent Applications EP 360018 and EP 204264.

The compound of formula 29 wherein $R_2$ is

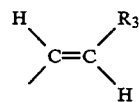

and $R_3$ is chloro, bromo, iodo, hydrogen, methyl or trifluoromethyl can be prepared from the compound of formula 43 wherein $R_2$ is iodo or —HgCl. Reaction of the compound of formula 43 wherein R₂ is iodo or —HgCl via organopalladium intermediates affords the compound of formula 43 wherein R₂ is

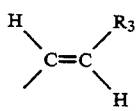

and R₃ is chloro, bromo, iodo, hydrogen, methyl or trifluoromethyl. The compound of formula 43 wherein R₂ is HgCl can be prepared from the compound of formula 31 wherein R₂ is hydrogen and P is a benzyl protecting group. See, for example, references in E. DeClercq et al., Pharmac. Ther., 26, 1 (1984); M. E. Perlman et al., J. Med. Chem., 28, 741 (1985); P. Herdewijn et al., J. Med. Chem., 28, 550 (1985); D. E. Bergstrom et al., J. Med. Chem., 27, 279 (1984).

Oxidation of a compound of formula 43 wherein R₂ is

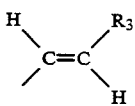

and R₃ is chloro, bromo, iodo, hydrogen, methyl, or trifluoromethyl, and subsequent treatment with zinc-/titanium tetrachloride/dibromomethane or methylenetriphenylphosphorane provides the corresponding compound of formula 44. Removal of the benzyl protecting groups from this compound using boron trichloride affords the compound of formula 29 wherein R₂ is

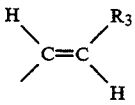

and R₃ is chloro, bromo, iodo, hydrogen, methyl or trifluoromethyl.

The compound of formula 36 wherein R₂ is

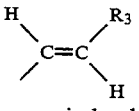

and R₃ is chloro, bromo, iodo, hydrogen, methyl or trifluoromethyl can be prepared from the corresponding compound of formula 29 by methods known in the art. See for example, T. S. Lin, et al., J. Med. Chem., 26, 1691 (1983); P. Herdewijn, et al., J. Med. Chem., 28, 550 (1985); European Patent Applications EP 360018 and EP 204264.

Alternatively, the compound of formula 36 wherein R₂ is

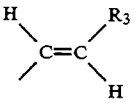

and R₃ is chloro, bromo, iodo, hydrogen, methyl or trifluoromethyl can be prepared from the corresponding compound of formula 44 using methods known in the art (and analogous to those used in the conversion of compound 33 to compound 37 wherein, for example, R₂ is hydrogen, methyl or ethyl), followed by removal of the benzyl protecting groups with boron trichloride.

The compound of formula 29 wherein R₂ is ethynyl can be prepared from a compound of formula 45 wherein R₂ is iodo and the protecting P₄ is acyl (e.g. acetyl), trityl, or substituted trityl as follows: Treatment of the compound of formula 45 wherein R₂ is iodo and P₄ is acyl with trimethylsilylacetylene/bis (triphenylphosphine) palladium (II) chloride/copper (I) iodide in triethylamine and, subsequently, with sodium methoxide in methanol according to procedures known in the art (see, for example, E. DeClercq et al., J. Med. Chem., 26, 661 (1983)) provides the compound of formula 43 wherein R₂ is ethynyl. Alternatively, analogous treatment of the compound of formula 45 wherein R₂ is iodo and P₄ is trityl or substituted trityl, followed by removal of the trityl or substituted trityl protecting group P₄, using, for example, aqueous acetic acid or aqueous alcoholic mineral acid, provides the compound of formula 43 wherein R₂ is ethynyl. Oxidation of the compound of formula 43 followed by methylenation with zinc-/titanium tetrachloride/dibromomethane or methylenetriphenylphosphorane yields the compound of formula 44 wherein R₂ is ethynyl, and subsequent removal of the benzyl protecting groups with boron trichloride provides the compound of formula 29 wherein R₂ is ethynyl.

The compound of formula 36 wherein R₂ is ethynyl can be prepared from the corresponding compound of formula 44 using methods known in the art (and analogous to those used in the conversion of compound 33 to compound 37 wherein, for example, R₂ is hydrogen, methyl, or ethyl), followed by removal of the benzyl protecting groups with boron trichloride.

Alternatively, the compound of formula 36 wherein R₂ is ethynyl can be prepared from the corresponding compound of formula 29 by methods known in the art. See, for example, T. S. Lin, et al., J. Med. Chem., 26, 1691 (1983); P. Herdewijn et al., J. Med. Chem., 28, 550 (1985); European Patent Applications EP 360018 and EP 204264.

Compounds of formula 1 wherein R₁ is

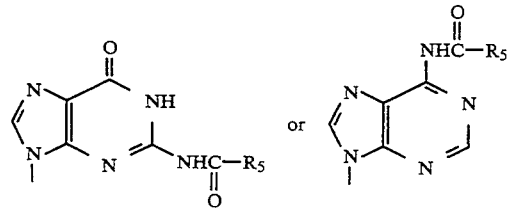

can be prepared from the corresponding compounds of formula 1 wherein R₁ is

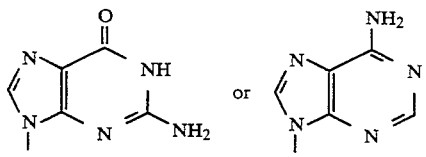

by methods known in the art.

Compounds of formula 1 wherein one or both R₆ and R₇ are

can be prepared by methods known in the art from the corresponding compounds of formula 1 wherein R₆ and R₇ are hydrogen.

For examples of acylation procedures see: "Synthetic Procedures in Nucleic Acid Chemistry", Vol. 1, W. W. Zorbach and R. S. Tipson, Eds., John Wiley and Sons, 1968; "Nucleic Acid Chemistry," Part 1, L. B. Townsend and R. S. Tipson, Eds., John Wiley and Sons, 1978; Y. Ishido, et al., *Nucleosides and Nucleotides*, 5, 159 (1986); J. C. Martin, et al., *J. Pharm. Sci.*, 76, 180 (1987); A. Matsuda, et al., *Synthesis*, 385 (1986).

Compounds of formula 1 wherein R₁ is

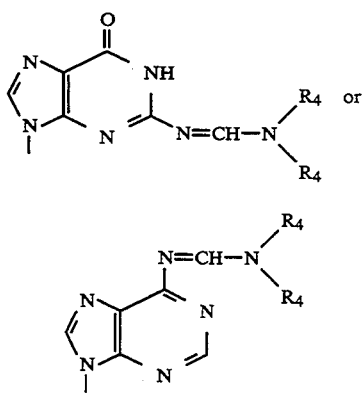

can be prepared from the corresponding compound of formula 1 wherein R₁ is

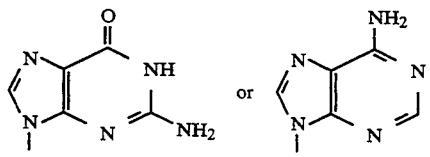

by procedures known in the art. See, for example, A. Holy and J. Zemlicka, *Collect. Czech. Chem. Commun.*, 32, 3159 (1967); K. K. Ogilvie, et al., *Nucleosides and Nucleotides*, 4, 507 (1985); M. H. Caruthers, et al., *J. Amer. Chem. Soc.*, 108, 2040 (1986).

Compounds of the formula 1 wherein R₆ and/or R₇ are —PO₃H₂ can be prepared from the corresponding compounds of formula 1 wherein R₆ and R₇ are hydrogen by procedures known in the art. See, for example, H. Schaller, et al., *J. Amer. Chem. Soc.*, 85, 3821 (1963); J. Beres, et al., *J. Med. Chem.*, 29, 494 (1986); R. Noyori, et al., *Tet. Lett.*, 28, 2259 (1987); W. Pfeiderer, et al., *Helv. Chim. Acta.*, 70, 1286 (1987); "Nucleic Acid Chemistry". Part 2, L. B. Townsend and R. S. Tipson, Eds., John Wiley and Sons, 1978.

Unless otherwise stated, the stereochemistry shown for the compounds of this invention and intermediates leading to compounds of this invention is absolute. It is drawn to show that in the compounds of this invention, the base represented by R₁ is cis to the —CH₂OR₆ substituent and trans to the —OR₇ substituent attached directly to the cyclopentyl ring. It is also drawn to show that the absolute stereochemistry of the cyclopentyl carbon attached to the base (R₁) is "S".

For example, the 1S-enantiomer of the compound of formula 1 wherein R₁ is

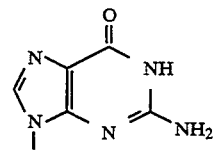

and R₆ and R₇ are hydrogen, [1S-(1α,3α,4β)]-2-amino1,9-dihydro-9-[4-hydroxy-3-(hydroxymethyl)-2methylenecyclopentyl]-6H-purin-6-one, can be prepared from the 1S-enantiomer of the compound of formula 2. The 1S-enantiomer of the compound of formula 2 can be prepared from the 1S-enantiomer of the compound of formula 3. By following the procedure described by K. Biggadike .et al., *J. Chem. Soc. Perkin Trans* 1, 549 (1988), the 1S-enantiomer of the compound of formula 3 can be prepared from the 1S-enantiomer of the compound of formula

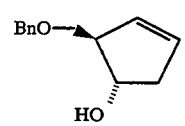

and the 1S-enantiomer of the compound of formula 46 can be prepared by reaction of the compound of formula

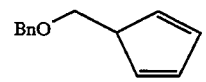

with the chiral hydroborating agent, (—)-diisopinocampheylborane [i.e. (—)-diisopinan-3-ylborane ].

The compounds of formula 1 wherein R₁ is

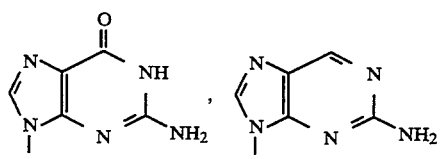

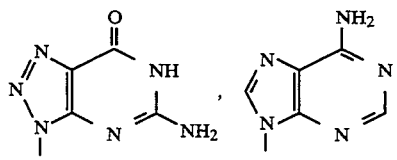

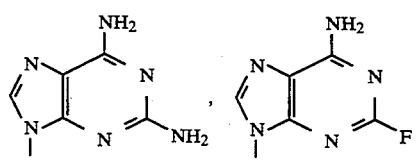

-continued

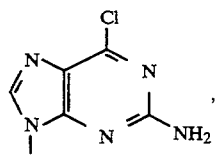

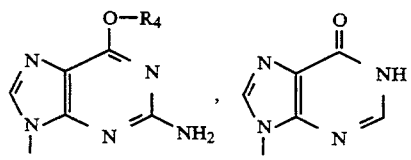

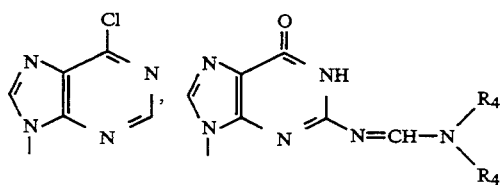

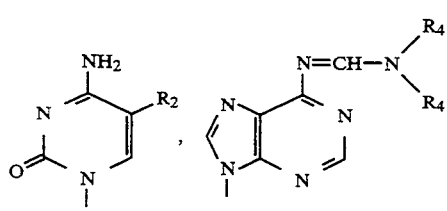

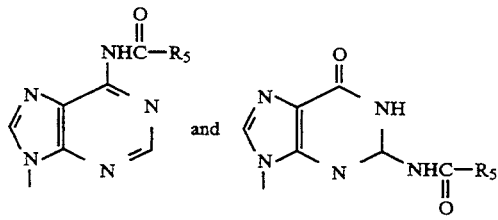

can form acid addition salts with inorganic or organic acids, Illustrative are the halide (e.g., chloride and bromide), alkylsulfonate, sulfate, phosphate and carboxylate salts.

The compounds of formula I wherein $R_1$ is

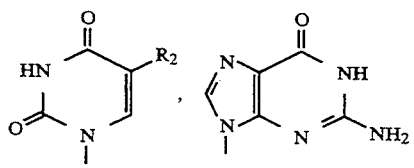

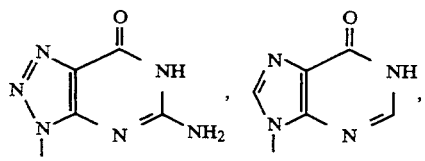

-continued

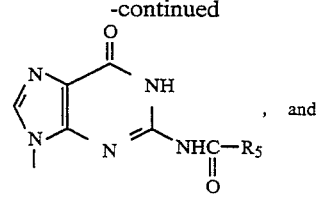, and

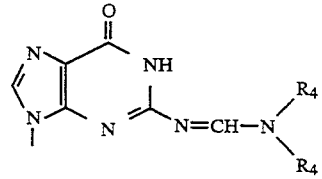

can form basic salts with inorganic and organic bases. Illustrative are alkali metal salts (e.g., sodium and potassium), alkaline earth metal salts (e.g. calcium and magnesium), ammonium and substituted ammonium salts.

The compounds of formula 1 wherein $R_6$ and/or $R_7$ are $-PO_3H_2$ can form basic salts with inorganic and organic bases. Illustrative are the alkali metal salts (e.g., sodium and potassium), alkaline earth metal salts (e.g., calcium and magnesium), ammonium and substituted ammonium salts.

The following examples are specific embodiments of this invention. All temperatures are given in degrees Centigrade.

EXAMPLE 1

[1S-(1α,3α,4β)]-2-Amino-1,9-dihydro-9-[4-hydroxy-3-(hydroxymethyl)-2-methylenecyclopentyl]-6-purin-6-one A. (−)-Diisopinocampheylborane (−)-Diisopinocampheylborane was prepared according to the procedure of H. C. Brown et al., *J. Org. Chem.*, 49, 945 (1984) starting with (1R)-(+)-α-pinene having $[α]$ $D^{23}$ +48° (neat).

(1R)-(+)-α-pinene (158.8 ml, 1 mol) was added to a stirred solution of 10M borane - methyl sulfide complex in methyl sulfide and 1000 ml of dry tetrahydrofuran at 0° under argon. After the addition, the flask was stoppered and left to stand at 5°. After 16 hours, additional (1R)-(+)-α-pinene (15.8 ml, 1 mol) was added, and the suspension was stirred for 8 hours at 5°. The solvents were removed by cannulation, and the residual solids were then washed with three 130 ml portions of dry ether (via cannulation) and dried in vacuo to give 205 g of (−)-diisopinocampheylborane.

B. (1S-trans)-2-[(Phenylmethoxy)methyl]-3-cyclopenten-1-ol

The known title compound and the title compounds in sections C and D were prepared by modification of the method of K. Biggadike et al., *J. Chem. Soc. Perkin Trans.* 1, 549 (1988). Cyclopentadiene (28.68 g, 0.434 mol), maintained at −30°, was added over 1 hour to a stirred mixture of 22.5 g of 40% sodium sand in mineral oil (0.391 g atm) in dry tetrahydrofuran (156 ml) at −10° under nitrogen. After the addition, the mixture was cannulated to an addition funnel at 0° C. and added over 1.3 hours to a stirred solution of benzyl chloromethyl ether (65.2 ml, 0,469 mol) in tetrahydrofuran (130 ml) at −50° under nitrogen. After the addition, the reaction was stirred at −45° for 1.3 hours and then cooled to −60°. Tetrahydrofuran (390 ml) was added followed by the above preparation of (−)- diisopinocampheylborane (136 g, 0,477 mol). The reaction was stirred for 1 hour at −60° C., warmed to −10° C. over 1.5 hours and then stirred for 16 hours at +5°. After concentrating the reaction mixture in vacuo to one half of its original volume, ether (390 ml) was added. The stirred mixture was cooled to 0° and then 3N sodium hydroxide (156 ml, 0,469 mol) was added over 45 minutes keeping the temperature at 0°. Then, 30% hydrogen peroxide (156 ml) was added over 1 hour while maintaining the temperature below 12°. After the addition, the reaction was stirred for 1 hour at 10°, and then the layers were separated. The aqueous layer was washed with ether (300 ml) and all ether layers were combined, washed with aqueous sodium chloride, dried (sodium sulfate), and concentrated in vacuo to a residue. Chromatography of the residue on a column of Merck silica gel (5000 ml) using petroleum ether-ether (2:1) gave a 10 g fraction of impure desired product, a 15.72 g fraction of pure desired product, and a 2.7 g fraction of impure desired product. The 10.0 g and 2.7 g fractions were combined with 4.7 g of impure desired product from several other similar reactions, and the mixture was chromatographed over 1500 ml of Merck silica gel, using petroleum ether-ether (2:1 and then 1:1), to give an additional 8.00 g of pure desired product.

C. [1S-(1α,2α,3β,5α)]-2-[(Phenylmethoxy)methyl]-6-oxabicyclo[3.1.0]hexan-3-ol

A solution of 3M t-butyl hydroperoxide in 2,2,4-trimethylpentane (87 ml, 0,261 mol) was added to a solution of (1S-trans)-2-[(phenylmethoxy)methyl]-3-cyclopenten-1-ol (29.63 g, 0.145 mol) and vanadyl acetylacetonate (400 mg) in dry dichloromethane (60 ml) under nitrogen over 75 minutes keeping the temperature at 25°. The mixture was stirred at room temperature for 16 hours and then cooled to 0°. Saturated aqueous sodium sulfite (150 ml) was added over 1 hour keeping the temperature below 20°, and the reaction was stirred at room temperature for 1.5 hours. The layers were separated, and the aqueous layer was extracted with dichloromethane (50 ml). The organic layers were combined, washed with water (50 ml), dried (sodium sulfate) and concentrated in vacuo to a residue. Chromatography of this residue on a column of Merck silica gel (2000 ml), eluting with a gradient of 33–50% ether in petroleum ether, afforded 24.19 g of pure desired product. Similar chromatography of impure fractions on Merck silica gel (400 ml) using petroleum ether-ether (1:1) gave an additional 2.71 g of desired product for a total yield of 26.90 g. The desired product had $[\alpha]_D^{22}$ +44.6° (c, 1.0, CHCl$_3$) and optical purity of ca. 87%. (See K. Biggadike et al., *J. Chem. Soc. Perkin Trans*, 1, 549 (1988).

D. [1S-(1α,2α,3β,5α)]-3-(Phenylmethoxy)-2-[(phenylmethoxy)methyl]-6-oxabicyclo[3.1.0]hexane To a mixture of 60% sodium hydride in mineral oil (5.11 g, 0.128 mmol) in dry tetrahydrofuran (247 ml) at room temperature under nitrogen was added, dropwise over twenty minutes, a solution of [1S-(1α,2α,3β,5α)]-2-[(phenylmethoxy)methyl]-6-oxabicyclo[3.1.0]hexan-3-ol (25.58 g, 0.116.mol) in tetrahydrofuran (123 ml). The mixture was stirred at room temperature for 2 hours and at 40° for 1 hour and then cooled to room temperature. Benzyl bromide (15.2 ml, 0.128 mol) and tetrabutylammonium iodide (412 mg) were added, and the reaction was stirred for 3 hours at room temperature. Ethanol (20 ml) was added, and after 10 minutes, the solvents were removed in vacuo. The residue was taken up in water (200 ml) and ether (200 ml) and the layers were separated. The aqueous layer was extracted with ether (200 ml) and the organic layers were combined, dried (sodium sulfate), and concentrated in vacuo to a residue. Chromatography of this residue on a column of Merck silica gel (2000 ml) using a gradient of 33–50% ether in petroleum ether afforded 27.21 g of desired product.

E. [1S-(1α,2β,3α,5β)-5-[2-Amino-6-(phenylmethoxy)-9H-purin-9-yl]-3-( phenylmethoxy)-2-[(phenylmethoxy)methyl]cyclopentanol Lithium hydride (80 mg, 10 mmol) was added to a stirred solution of [1S-(1α,2α,3β,5α)]-3-(phenylmethoxy)-2-[(phenylmethoxy)methyl]-6-oxa-bicyclo[3.1.0]hexane (6.2 g, 20 mmol) and 2-amino-6-(phenylmethoxy)-9H-purine (9.64 g, 40 mmol) in dry dimethylformamide (80 ml) at 60° under nitrogen. The temperature was increased to 125°, and the reaction was stirred at this temperature for 10 hours and then at room temperature for 6 hours. Acetic acid (572 μl, 10 mmol) was added, and after 10 minutes, the reaction mixture was concentrated in vacuo to a residue. Chromatography of this residue on a column of Merck silica gel (2000 ml) using a gradient of dichloromethane to 5% methanol in dichloromethane gave 9.03 g of partially purified desired product. Chromatography of this material on a column of SilicAR CC-7 (1000 ml) using a gradient of chloroform to 12% ethanol in chloroform afforded 6.63 g of pure desired product.

[1S-(1α,2β,3α,5β)]-5-[2-[[(4-Methoxyphenyl)diphenylmethyl]amino]-6-(phenylmethoxy)-9H-purin-9-yl]-3-(phenylmethoxy)-2-[(phenylmethoxy)methyl]cyclopentanol p-Anisylchlorodiphenylmethane (3.37 g, 10.9 mmol), triethylamine 2.35 ml, 16.8 mmol) and 4-dimethylaminopyridine (40 mg) were added to a solution of [1S-(1α,2β,3α,5β)-5-[2-amino-6-(phenylmethoxy)-9H-purin-9-yl]-3-phenylmethoxy)2-[(phenylmethoxy)methyl]cyclopentanol (5.45 g, 9.89 mmol) in dry dichloromethane (75 ml) under nitrogen, and the mixture was stirred at room temperature for 3 hours. The reaction was washed with 5% aqueous sodium bicarbonate (30 ml) and then water (10 ml), dried (sodium sulfate), and concentrated in vacuo to a residue. Chromatography of this residue on a column of SilicAR CC-7 (600 ml) packed in chloroform and eluting with chloroform-ethanol (99:1) gave 1.5 g of pure desired product. Chromatography of impure fractions on a column of SilicAR CC-7 (700 ml) packed in chloroform and eluting with chloroformethanol (99.5:0.5) afforded an additional 4.54 g of pure desired product.

G. [2R-(2α,3β,5α)-5-[2-[[(4-Methoxyphenyl)diphenylmethyl]amino]-6-(phenylmethoxy)-9H-purin-9-yl]-3-(phenylmethoxy)-2-8 (phenylmethoxy)methyl]-1-cyclopentanone To a solution of [1S-(1α,2β,3α,5β)]-5-[2-[[(4-methoxyphenyl)diphenylmethyl]amino]-6-(phenymethoxy)-9H-purin-9-yl]-3-(phenylmethoxy)-2-[(phenylmethoxy)methyl]cyclopentanol (4.10 g, 4.88 mmol, dried by concentration in vacuo from dry toluene) in dry dimethyl sulfoxide (12 ml) at room temperature under nitrogen was added 1,3-dicyclohexylcarbodiimide (3.08 g, 14.9 mmol) and methylphosphonic acid (0.239 g, 2.49 mmol). The reaction was stirred at room temperature for 4 hours, and then stored at −20° for 16 hours. After warming to room temperature, oxalic acid dihydrate (60 mg) in methanol (8 ml) was added, and the mixture was stirred for 2.5 hours. The reaction was filtered, and the filtrate was diluted with dichloromethane and water. The organic layer was washed with water (3×70 ml), dried (sodium sulfate), and concentrated in vacuo to a residue. The residue was taken up in dichloromethane (10 ml), filtered and concentrated in vacuo to a residue. (An $^1$HNMR spectrum indicated the presence of unreacted 1,3-dicyclohexylcarbodiimide). The residue was dissolved in dimethyl sulfoxide (9 ml) and then treated with methylphosphonic acid (150 mg) in methanol (6 ml) and oxalic acid dihydrate (60 mg). The mixture was stirred at room temperature for 4 hours and worked up as previously described to give crude desired product as a residue (3.73 g).

H. Zinc - Titanium Tetrachloride - Dibromomethane Complex (Preparation 1)

This complex was prepared according to the procedure of L. Lombardo, *Tetr. Let.*, 23, 4293 (1982). Titanium tetrachloride (11.5 ml, 0.105 mol) was slowly added dropwise to a stirred mixture of zinc dust (28.76 g, 0.44 mol) and dibromomethane (10.1 ml, 0.143 mol) in dry tetrahydrofuran (300 ml) at −40° under nitrogen. The mixture was warmed to 5° over 30 minutes, and then stirred at 5° for 4 days under argon. The slurry was stored at −20° under nitrogen and warmed to room temperature prior to use.

I. [1S-(1α,3α,4β)]-N-[(4-Methoxyphenyl)diphenylmethyl]-6-(phenylmethoxy)-9-[2-methylene-4-(phenylmethoxy)-3-[(phenylmethoxy)methyl]cyclopentyl]-9H-purin-2-amine To a solution of [2R-(2α,3β,5α)]-5-[2[[(4-methoxyphenyl)diphenylmethyl]amino]-6-(phenylmethoxy)-9H-purin-9-yl]-3-(phenylmethoxy)methyl]-1-cyclopentanone (1.80 g, 2.19 mmol) in dry dichloromethane (40 ml) under nitrogen was added a slurry of zinc - titanium tetrachloride - dibromomethane complex in tetrahydrofuran (Preparation 1, Example 1H) (40 ml, ca. 12.3 mmol). The mixture was stirred at room temperature for 3 hours, and slowly poured into a mixture of saturated aqueous sodium bicarbonate (200 ml) and dichloromethane (200 ml). After stirring for 20 minutes, the mixture was filtered through Celite. The Celite was washed with dichloromethane, and the layers in the filtrate were separated. The aqueous layer was extracted with dichloromethane, and the combined organic layers were dried (magnesium sulfate) and evaporated to a residue. The residue was taken up in dichloromethane and filtered through Celite. Concentration of the filtrate gave crude desired product as a residue (1.43 g).

J. [1S-(1α,3α,4β)]-2-Amino-1,9-dihydro-9-[2-methylene-4-(phenylmethyl)-3-[(phenylmethoxy)methyl]cyclopentyl]-6H-purin-6-one A mixture of crude [1S-(1α,3α,4β)]-N-[(4-methoxyphenyl)diphenylmethyl]-6-(phenylmethoxy)-9-[2-methylene-4-(phenylmethoxy)-3-[(phenylmethoxy)methyl]cyclopentyl]-9H-purin-2-amine (2.5 g), tetrahydrofuran (25 ml), methanol (25 ml) and 3N hydrochloric acid (12.5 ml) was heated at 50° for 2.5 hours and cooled to room temperature. The pH was adjusted to 7.3 with 1N potassium hydroxide, and the mixture was extracted with ethyl acetate (3×120 ml). The ethyl acetate extract was dried (sodium sulfate) and concentrated in vacuo to a residue, which was applied to a column of Merck silica gel (340 ml) packed in 3% ethanol in chloroform. Elution with a gradient of 3-20% ethanol in chloroform gave 316 mg of desired product as a residue.

K. [1S-(1α,3α,4β)]-2-Amino-1,9-dihydro-9-[4-hydroxy-3-(hydroxymethyl)-2-methylenecyclopentyl]-6H-purin-6-one To a stirred solution of [1S-(1α,3α,4β)]-2-amino-1,9-dihydro-9-[2-methylene-4-(phenylmethoxy)-3-[(phenylmethoxy)methyl]cyclopentyl]-6H-purin-6-one (304 mg, 0.673 mmol) in dry dichloromethane (12 ml) at −78° under nitrogen was added 1M boron trichloride in dichloromethane (6.7 ml, 6.7 mmol). The reaction was stirred at −78° for 2 hours and then at −40° for 30 minutes. After cooling the reaction to −78°, methanol (60 ml) was added slowly over 10 minutes. Upon warming to room temperature, the mixture was concentrated in vacuo, and then concentrated four times from 40 ml portions of methanol. The residue was dissolved in methanol (5 ml) and water (5 ml), and the pH was adjusted to 6.8 using 1N potassium hydroxide. After concentration in vacuo, the resulting slurry was applied as a suspension to a column of 16 ml of CHP-20P resin (Mitsubishi Chemical Industries Ltd., 75-150 micron) packed in water. Elution with a gradient of water to 3% acetonitrile in water and concentration of fractions in vacuo afforded the desired product as a solid (115 mg) having m.p. >220° and $[\alpha]_D^{22}+34°$ (c, 0.3, water).

Anal. calc'd. for $C_{12}H_{15}N_5O_3 \cdot 0.9\ H_2O$: C, 49.12; H, 5.77; N, 23.87 Found: C, 49.17; H, 5.87; N, 23.81.

EXAMPLE 2

[1S-(1α,3α,4β)]-1-[4-Hydroxy-3-(hydroxymethyl)-2-methylenecyclopentyl]-5-methyl-2,4 (1H,3H)pyrimidinedione A. [1S-(1α,2β,3α,4β)]-1-[2-Hydroxy-4-(phenylmethoxy)-3-[(phenylmethoxy)methyl]cyclopentyl]-5-methyl-2,4(1H,3H) -pyrimidinedione A mixture of 3.10 g (10 mmol) of [1S-(1α,2α,3β,5α)]-3-(phenylmethoxy)-2-[(phenylmethoxy)methyl]-6-oxabicyclo[3.1.0]hexane (dried by concentration in vacuo from three 10 ml portions of dry toluene) and thymine (2.52 g, 20 mmol) in 40 ml of dry dimethylformamide under argon was placed in an oil bath at 55° and stirred for 5 minutes. Sodium hydride (240 mg of 60% sodium hydride in mineral oil, 6 mmol) was added, and the temperature was increased to 140°. After 62 hours, the reaction was cooled to room temperature and quenched by addition of 0.45 ml of glacial acetic acid. The solvent was removed in vacuo (55°/1 mm), and the residue was triturated with dichloromethane and filtered. Evaporation of the filtrate gave a residue (4.93 g), which was applied to a column of Merck silica gel (140 g) packed in dichloromethane. Elution with dichloromethane and then 3% methanol in dichloromethane gave 1.89 g of pure desired product and 2.03 g of impure product. Chromatography of the 2.03 g fraction on 120 g of Merck silica gel using dichloromethane and then 3% methanol in dichloromethane provided 0.90 g of additional pure desired product for a total of 2.79 g.

B. [1S-(1α,3α,4β)]-5-Methyl-1-[2-oxo-4-(phenylmethoxy)-3-[(phenylmethoxy)methyl]cyclopentyl]-2,4(1H,3H)-pyrimidinedione To a solution of 2.74 g (6.28 mmol) of [1S-(1α,2β,3α,4β)]-1-[2-hydroxy-4-(phenylmethoxy)-3[(phenylmethoxy)methyl]cyclopentyl]-5-methyl-2,4-(1H,3H)-pyrimidinedione (dried by concentration in vacuo from two 25 ml portions of dry toluene) in 12.5 ml of dry dimethyl sulfoxide at room temperature under argon was added 3.88 g (18.8 mmol) of 1,3-dicyclohexylcarbodiimide and 0.301 g (3.14 mmol) of methylphosphonic acid. The reaction was stirred at room temperature for 3 hours, stored at −20° overnight, and stirred at room temperature for 2 hours. Methanol (2.5 ml) and oxalic acid dihydrate (25 mg) were added, and the reaction was stirred for 4 hours. The reaction mixture was filtered, and the solids were washed with dichloromethane. The filtrate was diluted to 250 ml with dichloromethane, washed with water (3×100 ml), dried (sodium sulfate) and evaporated to a residue (3.64 g). ($^1$HNMR analysis indicated some undecomposed 1,3-dicyclohexylcarbodiimide). The residue was dried by concentration in vacuo from 25 ml of dry toluene. To the dried residue was added 12 ml of dry dimethyl sulfoxide, 83 mg (0.86 mmol) of methylphosphonic acid, 6 ml of dry methanol, and 25 mg of oxalic acid dihydrate. The mixture was stirred at room temperature under argon for 4 hours, filtered and washed with dichloromethane. The filtrate was diluted with dichloromethane to 250 ml, washed with water (5×100 ml), dried (sodium sulfate), and evaporated to give 2.83 g of crude desired product as a residue.

C. [1S-(1α,3α,4β)]-5-Methyl-1-[2-methylene-4-(phenylmethoxy)-3-[(phenylmethoxy)methyl]cyclopentyl]-2,4(1H,3H)-pyrimidinedione To crude [1S-(1α,3α,4β)]-5-Methyl-1-[2-oxo-4-(phenylmethoxy)-3-[(phenylmethoxy)methyl]cyclopentyl]-2,4(1H,3H)-pyrimidinedione above (2.81 g) (dried by concentration in vacuo from three 25 ml portions of dry toluene) in 100 ml of dry dichloromethane under argon was added 41 ml of a slurry of zinc-titanium tetrachloride-dibromomethane complex in tetrahydrofuran (Preparation 1, Example 1H) (12.6 mmol). The reaction was stirred at room temperature for 4 hours, and then a 0.7 ml aliquot was removed. Saturated aqueous sodium bicarbonate solution (1 ml) was added to the aliquot, and the mixture was stirred at room temperature for 5 minutes. The mixture was extracted with dichloromethane (3x), and the dichloromethane extract was dried (magnesium sulfate) and evaporated to a residue. The residue was taken up in dichloromethane, filtered through Celite and evaporated to a residue, whose I.R. spectrum (dichloromethane) indicated a weak band at 1755–1745 cm$^{-1}$ indicative of starting ketone. Additional zinc-titanium tetrachloride-dibromomethane complex (10 ml, 3 mmol) was added to the reaction, and stirring was continued for 1.5 hours. Examination of the reaction by I.R. analysis indicated a very weak band at 1755–1745 cm$^{-1}$. The reaction was poured into 250 ml of saturated aqueous sodium bicarbonate solution and dichloromethane (250 ml), stirred vigorously for 15 minutes, and filtered through Celite. The layers in the filtrate were separated, and the aqueous layer was extracted with dichloromethane. The combined dichloromethane extracts were dried (magnesium sulfate) and evaporated to a residue, which was taken up in dichloromethane. After filtration, the dichloromethane was concentrated to a residue (2.44 g), which was applied to a column of Merck silica gel (200 g) packed in chloroform. Elution of the column with chloroform (1000 ml) and then ethyl acetate-chloroform (15:85) gave 690 mg of desired product as a residue.

D. [1S-(1α,3α,4β)]-1-[4-Hydroxy-3-(hydroxymethyl)-2-methylenecyclopentyl]-5-methyl-2,4(1H,3H)-pyrimidinedione To a stirred solution of [1S-(1α,3α,4β)]-5-methyl-1-[2-methylene-4-(phenylmethoxy)-3-[(phenylmethoxy)methyl]cyclopentyl]-2,4(1H,3H)-primidinedione (463 mg, 1.07 mmol) in 19 ml of dry dichloromethane at −70° under argon was added, over 5 minutes, 10.7 ml of 1M boron trichloride in dichloromethane. The reaction was warmed to −40° over 2.5 hours and then cooled to −70°. Dry methanol (20 ml) was added dropwise over 5 minutes, and then the cooling bath was removed. After stirring for 30 minutes, the reaction was concentrated in vacuo to a residue. The residue was concentrated four times from 20 ml portions of dry methanol and then dissolved in methanol (10 ml) and water (6 ml). The pH was adjusted to 7.0 using 0.5N potassium hydroxide, and the methanol was removed in vacuo. The aqueous suspension was applied to a column (32 ml) of CHP 20P resin packed in water. Elution with water, and then 5% and 10% methanol in water gave 194 mg of desired product as an amorphous residue. This residue was combined with an additional 70 mg of desired product from another run and lyophilized from water to give 215 mg of desired product having m.p. 52°–60° and $[\alpha]_D^{22}$+59° (c, 0.3, water)

Anal. calc'd. for $C_{12}H_{16}H_2O_4$. 0.4 $H_2O$: C, 55.53; H, 6.53; N, 10.80 Found: C, 55.49; H, 6.29; N, 10.84.

EXAMPLE 3

[1S-(1α,3α,4β)]-4-Amino-1-[4-hydroxy-3-hydroxymethyl)-2-methylenecyclopentyl]-2(1H) -pyrimidinone

[1S-(1α,2β,3α,4β)]-1-[2-Hydroxy-4-(phenylmethoxy)-3-[(phenylmethoxy)methyl]cyclopentyl]2,4(1H,3H)-pyrimidinedione To a solution of [1S-(1α,2α,3β,5α)]-3-(phenylmethoxy)-2-[(phenylmethoxy )methyl]-6-oxabicyclo[3.1.0-]hexane (3.28 g, 10.6 mmol) in dry dimethylformamide (40 ml) was added uracil (2.37 g, 21.2 mmol) and 60% sodium hydride in mineral oil (254 mg, 6.34 mmol). The suspension was heated at 140° for 5 days under nitrogen, and then cooled to room temperature. Acetic acid (1.2 ml) was added, and the solvents were removed in vacuo. Chromatography of the residue on a column of Merck silica gel (400 ml, packed in dichloromethane, eluting with a gradient of dichloromethane to 5% methanol in dichloromethane) afforded 2.68 g of desired product as a residue.

B. [1S-(1α,3α,4β)]-1-[2-Oxo-4-(phenylmethoxy )-3[(phenylmethoxy)methyl]cyclopentyl]-2,4(1H,3H)-pyrimidinedione A solution of [1S-(1α,2β,3α,4β)]-1-[2-hydroxy-4-(phenylmethoxy)-3-[(phenylmethoxy)methyl]cyclopentyl]-2,4(1H,3H)-pyrimidinedione (2.58 g, 6.11 mmol, dried by concentration in vacuo from dry toluene), 1,3-dicyclohexylcarbodiimide (3.77 g, 18.3 mmol) and methylphosphonic acid (293 mg, 3.05 mmol) in dry dimethyl sulfoxide (15 ml) was stirred at room temperature under nitrogen for 5 hours. Oxalic acid dihydrate (75 mg) in methanol (10 ml) was added, and the reaction was stirred for 4 hours and filtered. The precipitate was washed with dichloromethane (80 ml) and the filtrate and washes were combined, extracted with water (3×50 ml), dried (sodium sulfate), and concentrated in vacuo to a residue. The residue was dissolved in 20 ml of chloroform, filtered through Celite, and concentrated in vacuo to give 2.61 g of crude desired product.

C. [1S-(1α,3α,4β)]-1-[2-Methylene-4-(phenylmethoxy)-3-[(phenylmethoxy)methyl]cyclopentyl]-2,4(1H,3H)-pyrimidinedione A slurry of zinc-titanium tetrachloride-dibromomethane complex in tetrahydrofuran (Preparation 1, Example 1H) (45 ml, 13.5 mmol) was added to a solution of crude [1S-(1α,3α,4β)]-1-[2-oxo-4-(phenylmethoxy)-3-[(phenylmethoxy)methyl]cyclopentyl]-2,4(1H,3H)-pyrimidinedione (2.61 g, dried by concentration in vacuo from dry toluene) in dry dichloromethane (40 ml), and the mixture was stirred for 3 hours under nitrogen at room temperature. Additional 0.3M zinc-titanium tetrachloride-dibromomethane complex (10 ml) was added, and the reaction was stirred for 3 hours at room temperature and then stored at $-80°$ for 16 hours. The reaction was warmed to room temperature and poured into saturated aqueous sodium bicarbonate (250 ml) and dichloromethane (250 ml). The mixture was stirred for 1 hour and then filtered through Celite. The layers in the filtrate were separated, and the organic layer was extracted with water ($2\times 100$ ml). All organic layers were combined, dried (sodium sulfate) and concentrated in vacuo to a residue (2.5 g). Chromatography of this residue on Merck silica gel (400 ml, packed in chloroform) by elution with a gradient of chloroform to 30% ethyl acetate in chloroform gave 700 mg of desired product as a residue.

D. [1S-(1α,3α,4β)]-1-[2-Methylene-4-(phenylmethoxy)-3-[(phenylmethoxy)methyl]cyclopentyl]-4-(1H-1,2,4-triazol-1-yl)-2(1H)-pyrimidinone To a stirred solution of [1S-(1α,3α,4β)]-1-[2-methylene-4-(phenylmethoxy)-3-[(phenylmethoxy)methyl]cyclopentyl]-2,4(1H,3H)-pyrimidinedione (494 mg, 1.18 mmol) in dry pyridine (4 ml) at room temperature under nitrogen was added 4-chlorophenyl dichlorophosphate (518 μl, 3.19 mmol). After 5 minutes, 1,2,4-triazole (448 mg, 6.49 mmol) was added and the reaction was stirred for 5 days. The solvents were removed in vacuo, and the residue was dissolved in dichloromethane (100 ml) and extracted with water ($2\times 20$ ml) and 5% sodium bicarbonate ($2\times 20$ ml). The organic layer was dried (sodium sulfate) and concentrated in vacuo to give 586 mg of crude desired product.

E. [1S-(1α,3α,4β)]-4-Amino-1-[2-methylene-4-(phenylmethoxy)-3-[(phenylmethoxy)methyl]cyclopentyl]-2(1H)-pyrimidinone Concentrated ammonium hydroxide (12 ml) was added to a solution of crude [1S-(1α,3α,4β)]-1-[2-methylene-4-(phenylmethoxy)-3-[(phenylmethoxy)methoxy)methyl]cyclopentyl]-4-(1H-1,2,4-triazol-1-yl)-2(1H)-pyrimidinone (586 mg) in dioxane (12 ml, purified by passage through basic alumina). The reaction was stirred at room temperature under nitrogen for 16 hours. Additional ammonium hydroxide (1 ml) was added, and reaction was stirred for 3 hours longer. After removal of solvents in vacuo, the residue was dissolved in dichloromethane (75 ml). The dichloromethane solution was extracted with 5% sodium hydroxide ($2\times 20$ ml), dried (sodium sulfate), and concentrated in vacuo to a residue. Chromatography of this residue on a column of Merck silica gel (100 ml, packed in chloroform) by elution with a gradient of 2% to 8% methanol in chloroform gave 177 mg of desired product as a residue.

F. [1S-(1α,3α,4β)]-4-Amino-1-[4-hydroxy-3-hydroxymethyl)-2-methylenecyclopentyl]-2(1H)-pyrimidinone To a solution of [1S-(1α,3α,4β)]-4-amino-1-[-2-methylene-4-(phenylmethoxy)-3-[(phenylmethoxy)methyl]cyclopentyl]-2(1H)-pyrimidinone ( 164 mg, 0,393 mmol) in dry dichloromethane (8 ml) at $-78°$ under nitrogen was added, over 3 minutes, 1M boron trichloride in dichloromethane (3.93 ml, 3.93 mmol). The reaction was stirred for 1.5 hours at $-78°$, and then methanol (9 ml) was added over 5 minutes. After warming the reaction to room temperature over 20 minutes, the solvents were removed in vacuo, and the residue was concentrated from methanol ($3\times 15$ ml). The residue was dissolved in water and methanol, and the pH was adjusted to 7 using 1N potassium hydroxide. The methanol was removed in vacuo, and the aqueous slurry was applied to a column of CHP 20P resin (70 ml) packed in water. Elution of the column with a gradient of water to 20% methanol in water gave 48 mg of desired product as a solid having m.p. $75°-78°$ and $[\alpha]_D^{22}$ $+51°$ (c, 0.29, water).

Anal. calc'd. for $C_{11}H_{15}N_3O_3 \cdot 1.34 H_2O$: C, 50.56; H, 6.82; N, 16.08 Found: C, 50.58; H, 6.31; N, 16.06.

EXAMPLE 4

[1S-(1α,3α,4β)]-1-[4-Hydroxy-3-(hydroxymethyl)-2-methylenecyclopentyl]-5-iodo-2,4(1H,3H)pyrimidinedione A. [1S-(1α,2β,3α,4β)]-1-[2-Hydroxy-4-(phenylmethoxy)-3-[(phenylmethoxy)methyl]cyclopentyl]-5-iodo-2,4(1H,3H)-pyrimidinedione To a solution of [1S-(1α,2β,3α,4β)]-1-[2-hydroxy-4-(phenylmethoxy)-3-[(phenylmethoxy)methyl]cyclopentyl]-2,4(1H,3H)-pyrimidinedione (1.32 g, 3.12 mmol) in dry dioxane (50 ml) was added iodine 1.59 gm 6.25 mmol) and 0.8N nitric acid (4.1 ml, 3.34 mmol). The reaction was heated at 90° for 3 hours, and after cooling the reaction to room temperature, a saturated solution of sodium thiosulfate was added until a light orange color persisted. Water (50 ml) was added, and the mixture was extracted with dichloromethane ($3\times 70$ ml). The organic extract was dried (sodium sulfate) and concentrated in vacuo to a residue. Chromatography of this residue on a column of Merck silica gel (100 ml, packed in dichloromethane) using a gradient of dichloromethane to 3% ethanol in dichloromethane gave 895 mg of desired product as a residue.

B. [1S-(1α,3α,4β)]-5-Iodo-1-[2-oxo-4-(phenylmethoxy)-3-[(phenylmethoxy)methyl]cyclopentyl]-2,4(1H,3H)-pyrimidinedione A solution of [1S-(1α,2β,3α,4β)]-1-[2-hydroxy-4-(phenylmethoxy)-3-[(phenylmethoxy)methyl]cyclopentyl]-5-iodo-2,4(1H,3H)-pyrimidinedione (687 mg, 1.25 mmol, dried by concentration in vacuo from dry toluene) in dry dichloromethane (4 ml) was added to a suspension of pyridinium dichromate (801 mg, 2.13 mmol, dried in vacuo over phosphorus pentoxide) and crushed 3A molecular sieves (801 mg, dried at 325°). The reaction was stirred at room temperature under nitrogen for 2 hours, and filtered through Whatman #1 filter paper. The precipitate was washed with dichloromethane, and the filtrate was concentrated in vacuo to a residue, which was sonicated in 30 ml of ethyl acetate. Filtration of the mixture through a 0.2 μm Nylon filter (Rainin 66) layered with Celite and glass wool, and concentration in vacuo gave 544 mg of crude desired product as a residue.

C. Zinc-Titanium Tetrachloride-Dibromomethane Complex (Preparation 2)

This complex was prepared by a modification of the procedure of L. Lombardo, Tetr. Let., 23, 4293 (1982). Titanium tetrachloride (5.75 ml, 0.0523 mol) was slowly added dropwise to a stirred mixture of zinc dust (10.59 g, 0.162 mol) and dibromomethane (4.96 ml, 0.071 mol) in dry tetrahydrofuran (150 ml) at $-40°$ under nitrogen. After the addition, the mixture was warmed to 5° over 30 minutes and then stirred at 5° under argon for 4 days.

The slurry was stored at −20° under argon and warmed to room temperature prior to use.

D. [1S-(1α,3α,4β)]-5-Iodo-1-[2-methylene-4-(phenylmethoxy)-3-[(phenylmethoxy)methyl]cyclopentyl]-2,4(1H,3H)-pyrimidinedione To a solution of [1S-(1α,3α,4β)]-5-iodo-1-[2-oxo-4-(phenylmethoxy)-3-[(phenylmethoxy)methyl]cyclopentyl]-2,4(1H,3H)-pyrimidinedione (428 mg, 0.783 mmol, dried by concentration in vacuo from dry toluene and tetrahydrofuran) in dry dichloromethane (9.5 ml) was added the slurry of zinc-titanium tetrachloride-dibromomethane complex in tetrahydrofuran (Preparation 2, Example 4C) (7.83 ml, 2.35 mmol). The mixture was stirred at room temperature under nitrogen for 3 hours, and then it was slowly poured into a mixture of saturated sodium bicarbonate (100 ml) and dichloromethane (75 ml). The mixture was stirred for 1 hour and filtered through Celite using dichloromethane. The layers in the filtrate were separated, and the aqueous layer was extracted with ethyl acetate. The organic layers were combined, dried (sodium sulfate), and concentrated in vacuo to a residue. Chromatography of the residue on a column of Merck silica gel (100 ml, packed in dichloromethane) using a gradient of 1% to 5% ethanol in dichloromethane afforded 243 mg of desired product as a residue.

E. 1S-(1α,3α,4β)]-1-[4-Hydroxy-3-(hydroxymethyl)-2-methylenecyclopentyl]-5-iodo-2,4(1H,3H)-pyrimidinedione To a solution of [1S-(1α,3α,4β)]-5-iodo-1-[2-methylene-4-(phenylmethoxy)-3-[(phenylmethoxy)methyl]cyclopentyl]-2,4(1H,3H)-pyrimidinedione (200 mg, 0.368 mmol, dried by concentration from toluene) in dichloromethane (7.5 ml) at −78° under nitrogen was added, over 3 minutes, 1M boron trichloride in dichloromethane (3.68 ml, 3.68 mmol). The reaction was stirred for 2 hours at −78°, and then methanol (10 ml) was added over 5 minutes. The reaction was warmed to room temperature over 20 minutes and evaporated in vacuo to a residue. The residue was concentrated from methanol (3×10 ml) and dissolved in methanol and water. The pH was adjusted to 7.1, using 0.1M potassium hydroxide, and the mixture was concentrated to remove methanol and applied to a column of CHP 20P resin (50 ml) packed in water. Elution with a gradient of water to 50% methanol in water gave 69 mg of desired product as a solid, which was combined with 9 mg of additional desired product from a similar smaller scale reaction to give 78 mg of desired product as a solid having m.p. 180° (dec.) and $[\alpha]_D^{22}+63°$ (c, 0.29, methanol).

Anal. calc'd. for $C_{11}H_{13}IN_2O_4$. 0.32 $H_2O$: C, 35.72; H, 3.72; N, 7.58 Found: C, 35.97; H, 3.55; N, 7.32.

EXAMPLE 5

[1S-[1α(E),3α,4β)]-5-(2-Bromoethenyl)-1-[4-hydroxy-3-(hydroxymethyl)-2-methylenecyclopentyl]-2,4(1H,3H)-pyrimidinedione A. [1S-[1α(E),2β,3α,4β)]-3-[1,2,3,4-Tetrahydro-1-[2-hydroxy-4-(phenylmethoxy)-3-[(phenylmethoxy)methyl]cyclopentyl]-2,4-dioxo-5-pyrimidinyl]-2-propenoic acid, methyl ester A mixture of palladium(II) acetate (0.195 g, 0.871 mmol), triphenylphosphine (0.456 g, 1.74 mmol) and triethylamine (2.56 ml, 0.0183 mol) in dioxane (200 ml, purified on basic alumina and degassed in vacuo) was heated for 10 minutes at 90° under nitrogen. A solution of [1S-(1α,2β,3α,4β)]-1-[2-hydroxy-4-(phenylmethoxy)-3-[(phenylmethoxy)methyl]cyclopentyl]-5-iodo-2,4(1H,3H)-pyrimidinedione (6.70 g, 0.0122 mol, dried by concentration in vacuo from dry toluene) and methyl acrylate (3.23 ml, 0.0366 mol) in degassed dioxane (20 ml) was added, and the reaction was heated at 90° for 4.5 hours. Celite (5 g) was added, and after stirring at 90° for 15 minutes, the hot slurry was filtered through Celite and washed with chloroform (80 ml). The filtrate and the wash were combined and concentrated in vacuo to a residue, which was dissolved in chloroform (400 ml). The chloroform was washed with water (100 ml), dried (sodium sulfate) and concentrated in vacuo to a residue. Chromatography of the residue on a column of Merck silica gel (800 ml, packed in dichloromethane) by eluting with a gradient of chloroform to 5% ethanol in chloroform gave 2.21 g of desired product as a residue.

B. [1S-[1α(E),2β,3α,4β)]-3-[1,2,3,4-Tetrahydro-1-[2-hydroxy-4-(phenylmethoxy)-3-[(phenylmethoxy)methyl]cyclopentyl]-2,4-dioxo-5-pyrimidinyl]-2-propenoic acid A solution of [1S-[1α(E),2β,3α,4β)]-3-[1,2,3,4-tetrahydro-1-[2-hydroxy-4-(phenylmethoxy)-3-[(phenylmethoxy)methyl]cyclopentyl]-2,4-dioxo-5-pyrimidinyl]-2-propenoic acid, methyl ester (2.98 g, 5.88 mmol), tetrahydrofuran (45 ml), and 2N potassium hydroxide (29.4 ml, 58.8 mmol) was stirred at room temperature under nitrogen for 2.5 hours. After cooling the mixture to 0°, the pH was adjusted to 2 using 6N hydrochloric acid. The tetrahydrofuran was removed in vacuo, and the mixture was diluted with water and extracted with ethyl acetate (3×200 ml). The ethyl acetate extract was dried (sodium sulfate), and concentrated in vacuo to give 3.14 g of desired product as a residue.

C. [1S-[1α(E),2β,3α,4β)]-5-(2-Bromoethenyl)-1-[2-hydroxy-4-(phenylmethoxy)-3-[(phenylmethoxy)methyl]cyclopentyl]-2,4(1H,3H)-pyrimidinedione Potassium bicarbonate (1.76 g, 17.64 mmol) and N-bromosuccinimide (1.05 g, 5.88 mmol) were added to a solution of [1S-[1α(E),2β,3α,4β)]-3-[1,2,3,4-tetrahydro-1-[2-hydroxy-4-(phenylmethoxy)-3-[(phenylmethoxy)methyl]cyclopentyl]-2,4-dioxo-5-pyrimidinyl]-2-propenoic acid (2.89 g, 5.88 mmol, dried by concentration in vacuo from dry dimethylformamide) in dry dimethylformamide (35 ml), and the mixture was stirred at room temperature under nitrogen for 2 hours. Filtration of the reaction mixture and concentration of the filtrate in vacuo gave a residue, which was chromatographed on a column of Merck silica gel (400 ml, packed in dichloromethane) by elution with a gradient of dichloromethane to 5% ethanol in dichloromethane to give a 1.59 g fraction containing desired product and succinimide and a 620 mg fraction consisting of crude desired product. Chromatography of the 620 mg fraction on Merck silica gel (100 ml in dichloromethane), using the aforementioned gradient, gave a fraction containing 120 mg of desired product and succinimide. The 1.59 g fraction and the 120 mg fraction were dissolved in dichloromethane (100 ml), and the solution was washed with dilute sodium thiosulfate (50 ml), 1M potassium bicarbonate (3×50 ml) and water (50 ml), dried (sodium sulfate) and concentrated in vacuo to give to give 1.56 g of pure desired product.

D. [1S-[1α(E),3α,4β)]-5-(2-Bromoethenyl)-1-[2-oxo-4-(phenylmethoxy)-3-[(phenylmethoxy)methyl]cyclopentyl]-2,4(1H,3H)-pyrimidinedione 1,3-Dicyclohexylcarbodiimide (1.55 g, 7.5 mmol) and methylphosphonic acid (120 mg, 1.25 mmol) were added to a solution of [1S-[1α(E),2β,3α,4β]]-5-(2-bromoethenyl)-1-[2-hydroxy-4-(phenylmethoxy)-3-[(phenylmethoxy)methyl]cyclopentyl]-2,4(1H,3H)pyrimidinedione (1.32 g, 2.5 mmol, dried by concentration in vacuo from dry toluene) in dry dimethyl sulfoxide (10 ml), and the mixture was stirred at room temperature under nitrogen for 5 hours. A solution of oxalic acid dihydrate (30 mg) in methanol (4 ml) was added, and stirring was continued for 2 hours. The reaction was filtered, and the precipitate was washed with dichloromethane. The combined filtrate and wash (ca. 80 ml) was washed with water (4×40 ml), dried (sodium sulfate), and concentrated in vacuo to give 1.45 g of crude desired product as a residue.

E. [1S-[1α(E),3α,4β]]-5-(2-Bromoethenyl )-1-[2-methylene-4-(phenylmethoxy )-3-[(phenylmethoxy)methyl]cyclopentyl]-2,4(1H,3H)-pyrimidinedione To a solution of [1S-[1α(E),3α,4β]]-5-(2-bromoethenyl)-1-[2-oxo-4-(phenylmethoxy)-3[(phenylmethoxy)methyl]cyclopentyl]-2,4(1H,3H)-pyrimidinedione (1.45 g crude, dried by concentration in vacuo from dry toluene) in dry dichloromethane (30 ml) was added a slurry of zinc titanium tetrachloride-dibromomethane complex in tetrahydrofuran (Preparation 2, Example 4C) (25 ml, 7.5 mmol). The reaction was stirred at room temperature under nitrogen for 5 hours and poured into a mixture of saturated sodium bicarbonate (200 ml) and dichloromethane (200 ml). After stirring for 45 minutes, the mixture was filtered through Celite. The layers in the filtrate were separated, the organic layer was washed with water (200 ml), dried (sodium sulfate), and concentrated in vacuo to a residue. Chromatography of the residue on a column of Merck silica gel (600 ml, packed in chloroform) using a gradient of chloroform to 15% ethyl acetate in chloroform afforded 400 mg of a solid consisting of 362 mg of desired product and 38 mg of 1,3-dicyclohexylurea.

F. 1S-[1α(E),3α,4β]]-5-(2-Bromoethenyl)-1-[4-hydroxy-3-hydroxymethyl)-2-methylenecyclopentyl]-2,4(1H,3H)-pyrimidinedione To a solution of the above preparation containing 362 mg (0.769 mmol) of [1S-[1α(E),3α,4β]]-5-(2-bromoethenyl)-1-[2-methylene-4-(phenylmethoxy)-3-[(phenylmethoxy)methyl]cyclopentyl]-2,4(1H,3H)pyrimidinedione (dried by concentration in vacuo from dry toluene) in 10 ml of dry dichloromethane at −78° under nitrogen was added 1M boron trichloride in dichloromethane (7.69 ml, 7.69 mmol). The mixture was stirred at −78° for 1 hour, and then methanol (12 ml) was slowly added. After warming the solution to room temperature over 30 minutes, the solvents were removed in vacuo leaving a residue, which was concentrated in vacuo from methanol (2×20 ml). The residue was taken up in methanol and water, the pH was adjusted to 7 using 0.1N potassium hydroxide. After concentration in vacuo to remove methanol, the aqueous suspension was applied to a column of CHP 20P resin (40 ml, packed in water). Elution of the column with a gradient of water to 50% methanol-water afforded 78 mg of pure desired product and 92 mg of impure material. Chromatography of the 92 mg fraction on CHP 20P resin (40 ml, packed in water) using a gradient of 30–60% methanol in water provided an additional 21 mg of pure desired product for a total yield of 99 mg of desired product having m.p. >220° and $[α]_D^{22}$ +62° (c, 0.3, methanol).

Anal. calc'd. for $C_{13}H_{15}N_2O_4Br$. 1.5 $H_2O$: C, 44.81; H, 4.51; N, 8.04 Found: C, 44.94; H, 4.31; N, 7.91.

EXAMPLE 6

[1R-(1α,3α,5β)]-3-(6-Amino-9H-purin-9-yl)-5-hydroxy-2-methylenecyclopentanemethanol A. [1S-(1α,2α,3α,5β)]-5-(6-Amino-9H-purin-9-yl)-3-(phenylmethoxy)-2-[(phenylmethoxy)methyl]-cyclopentanol To [1S-(1α,2α,3β,5α)]-3-(phenylmethoxy)-2-[(phenylmethoxy)methyl]-6-oxabicyclo[3.1.0]hexane (1.82 g, 5.85 mmol, dried by concentration in vacuo from dry toluene) in 41 ml of dry dimethylformamide under argon was added 1.58 g (11.7 mmol) of adenine followed by 31 mg (3.9 mmol) of lithium hydride. The stirred mixture was placed in a bath at 60° and the temperature was increased to 130°. After 19 hours at 130°, the mixture was cooled to 40°, and acetic acid (0.29 ml, 5 mmol) was then added. The dimethylformamide was removed in vacuo, and the residue was triturated with dichloromethane. Filtration of this triturate gave 1.60 g of insolubles and 3.01 g of a residue from concentration of the filtrate. Chromatography of the 3.01 g fraction on a column of Merck silica gel (160 g, packed in dichloromethane) by eluting with dichloromethane and then 3% methanol in dichloromethane afforded 1.26 g of desired product as a residue. Trituration of the 1.60 g fraction with dichloromethane, filtration, and evaporation of the filtrate gave 77 mg of additional desired product as a residue.

B. [1S-(1α,2β,3α,5β)]-5-[6-(Acetylamino)-9H-purin-9-yl]-3-(phenylmethoxy)-2-[(phenylmethoxy)methyl]cyclopentanol To a stirred solution of [1S-(1α,2β,3α,5β)]-5-(6-amino-9H-purin-9-yl)-3-(phenylmethoxy)-2-[(phenylmethoxy)methyl]cyclopentanol (1.33 g, 3 mmol, dried by concentration in vacuo from dry pyridine) in dry pyridine (15 ml) at room temperature under argon was added, dropwise, chlorotrimethylsilane (1.91 ml, 15 mmol). After 30 minutes, acetic anhydride (1.41 ml, 15 mmol) was added, and the mixture was stirred at room temperature for 3 hours. The mixture was cooled to 0°–5°, and water (3 ml) was added dropwise. Stirring was continued for 5 minutes, and then 29% ammonium hydroxide (3 ml) was added. After stirring for 25 minutes, the mixture was concentrated in vacuo to a residue, which was taken up in dichloromethane and 5% aqueous potassium bicarbonate. The layers were separated, and the aqueous layer (pH 7.5) was extracted with dichloromethane (3X). The dichloromethane layers were combined, washed with 5% potassium bicarbonate, dried (sodium sulfate) and concentrated in vacuo to a residue. Chromatography of this residue on a column of Merck silica gel (130 g, packed in dichloromethane) by elution with a gradient of dichloromethane to 5% methanol in dichloromethane gave 1.23 g of desired product as a residue.

C. [2R-(2α,3β,5α)]-5-[6-(Acetylamino)-9H-purin-9-yl]-3-(phenylmethoxy)-2-[(phenylmethoxy)methyl]cyclopentanone 1,3-Dicyclohexylcarbodiimide (773 mg, 3.75 mmol) and methylphosphonic acid (60 mg, 0.63 mmol) were added to a solution of [1S-(1α,2β,3α,5β)]-5-[6-(acetylamino)-9H-purin-9-yl]-3-(phenylmethoxy)-2-[(phenylmethoxy)methyl]cyclopentanol (610 mg, 1.25 mmol, dried by concentration in vacuo from dry dichloromethane-toluene (1:1)) in 2 ml of dry dimethyl sulfoxide, and the mixture was stirred at room temperature under argon. After 4 hours, dry methanol (1.5 ml) and oxalic acid dihydrate (15 mg) were added, and the mixture was stored at −20° under nitrogen for 16 hours. The mixture was then stirred at room temperature under argon for 4 hours and filtered using dichloromethane. Evaporation of the filtrate gave a residue, which was taken up in dichloromethane. The dichloromethane solution was washed with water, dried (sodium sulfate), and concentrated in vacuo to a residue. Addition of dichloromethane, followed by filtration and concentration in vacuo afforded 629 mg of crude desired product as a residue.

D. [1S-(1α,3α,4β)]-9-[2-Methylene-4-(phenylmethoxy)-3-[(phenylmethoxy)methyl]cyclopentyl]-9H-purin-6-amine To a solution of [2R-(2α,3β,5α)]-5-[6-(acetylamino)-9H-purin-9-yl]-3-(phenylmethoxy)-2-[(phenylmethoxy)methyl]cyclopentanone (629 mg, dried by concentration in vacuo from dry tetrahydrofuran-toluene (1:1)) in 20 ml of dry dichloromethane at room temperature under argon was added 12.5 ml of a slurry of zinc titanium tetrachloride-dibromomethane complex in tetrahydrofuran (Preparation 1, Example 1H) (3.75 mmol). The mixture was stirred for 4 hours and poured into saturated sodium bicarbonate (80 ml). Dichloromethane (80 ml) was added, and the mixture was stirred at room temperature for 50 minutes. The mixture was filtered through Celite, using dichloromethane, and the layers in the filtrate were separated. The aqueous layer was extracted with dichloromethane and all dichloromethane layers were combined, dried (magnesium sulfate) and concentrated in vacuo to a residue. Chromatography of the residue on a column of Merck silica gel (38 g, packed in dichloromethane) by elution with a gradient of dichloromethane to 3% methanol in dichloromethane gave 48 mg of pure desired product and 173 mg of impure desired product. Chromatography of the 173 mg fraction on a column of Merck silica gel (13 g) using the aforementioned gradient gave an additional 28 mg of desired product as a residue for a total yield of 76 mg of desired product.

E. [1R-(1α,3α,5β)]-3(6-Amino-9H-purin-9-yl )-5-hydroxy-2-methylenecyclopentanemethanol A solution of 1M boron trichloride in dichloromethane (3.2 ml, 3.2 mmol) was added dropwise over 4 minutes to a stirred solution of [1S-(1α,3α,4β)]-9-[2-methylene-4-(phenylmethoxy)-3-[(phenylmethoxy)methyl]cyclopentyl]-9H-purin-6-amine (142 mg, 0.32 mmol) in 6.5 ml of dry dichloromethane at −70° under argon, and the mixture was stirred at −70° for 1.5 hours. Dry methanol (6 ml) was added over 3 minutes, and then the mixture was warmed to room temperature and concentrated in vacuo to a residue. The residue was concentrated in vacuo from three 6 ml portions of methanol and then taken up in methanol (4 ml) and water (2 ml). The pH was adjusted to 8.8 using 1N potassium hydroxide, and the mixture was concentrated to a residue, which was applied as a suspension in water to a column of CHP-20P resin (17 ml, packed in water). Elution with a gradient of water to 20% methanol in water afforded, after lyophilization, 35 mg of desired product as a solid having m.p. 52°-58°.

EXAMPLE 7

1S-[1α(E),3α,4β)]-1-[4-Hydroxy-3-(hydroxymethyl)-2-methylenecyclopentyl]-5-(2-iodoethenyl)-2,4(1H,3H)-pyrimidinedione A. (−)-Diisopinocampheylborane (−)-Diisopinocampheylborane was prepared using (1R)-(+)-α-pinene of optical purity 98 +% ($[\alpha]_D^{23}$+50.7° (neat)). A solution of 616 ml. of 1.0M borane tetrahydrofuran complex was added to (1R)-(+)-α-pinene (185 g., 1.36 mol.) at 0°-5° under nitrogen, and the reaction was stirred overnight at 5° to give the desired product as a crystalline slurry.

B. (1S-trans)-2-[(Phenylmethoxy)methyl]-3-cyclopenten-1-ol

Cyclopentadiene (39 g., 0.59 mol.) at −20° was added over 35 minutes to a stirred mixture of 31.0 g. of 40% sodium sand in mineral oil (0.54 g. atm.) in 264 ml. of dry tetrahydrofuran at −15°. The mixture was stirred at −10° for 1.5 hours, warmed to 0°, and cannulated to an addition funnel at 0°. The mixture was then added over 30 minutes to a stirred solution of benzyl chloromethyl ether (100 g., 0.64 mol.) in 200 ml. of tetrahydrofuran at −50° to −55°. The mixture was stirred at −55° to −40° for 1 hour and then cooled to −65°. To this was added, by cannula over 5 minutes, the crystalline slurry of (−)-diisopinocampheylborane from step A, which had been cooled to −60°. The reaction was stirred at −60° for 1 hour, warmed to −10° and stored at −20° overnight. The reaction mixture was stirred for 1 hour at 5° and concentrated in vacuo to one half its original volume. Ether (600 ml.) was added, the stirred mixture was cooled to 0°, and 188 ml. of 3N sodium hydroxide was added dropwise keeping the temperature below 5°. Cold 30% hydrogen peroxide (188 ml.) was added dropwise over 1 hour keeping the temperature below 12°, and then the mixture was stirred for 1 hour longer while maintaining the temperature below 12°. The layers were separated, and the aqueous layer was washed with ether. The ether extracts were combined, dried(-sodium sulfate), and concentrated in vacuo to a residue (337 g.). Chromatography of this residue on a column of Merck silica gel [2300 g., packed in petroleum ether-ether (2:1)] using petroleum ether-ether (2:1) and then (1:1)]gave fraction A (17.56 g. of impure desired product), fraction B (11.03 g. of pure desired product), and fraction C (3.52 g. of impure desired product). Similar chromatography of fraction A on 800 g. of silica gel, and fraction C on 140 g. of silica gel, gave 8.08 g. and 2.33 g., respectively, of additional pure desired product for a total yield of 21.44 g. of title compound.

C. [1S-(1α,2α,3β,5α)]2-[(Phenylmethoxy)methyl]-6-oxabicyclo[3.1.0]hexan-3-ol

The title compound was prepared by following the procedure in Example 1C, but using the preparation of (1S-trans)-2-[(phenylmethoxy)methyl]-3-cyclopenten-1-ol from step B above. This afforded the title compound with $[\alpha]_D^{22}$+48.0° (c, 1.0, CHCl₃) and optical purity of 94%. [See S. K. Biggadike et al., J. Chem. Soc. Perkin Trans, 1, 549 (1988)].

D. [1S-(1α,2α,3β,5α)]-3-(Phenylmethoxy)-2-[(phenylmethoxy)methyl]-6-oxabicyclo[3.1.0]-hexane The title compound was prepared by following the procedure in Example 1D, but using the preparation of [1S-(1α,2α,3β,5α)]-2-[(phenylmethoxy)methyl]-6-oxabicyclo[3.1.0]hexan-3-ol from step C above.

E. [1S-(1α, 2β,3α,4β)]-1-[2-Hydroxy-4-(phenylmethoxy)-3-[(phenylmethoxy)methyl]cyclopentyl]-2,4(1H,3H)-pyrimidinedione The title compound was prepared by following the procedure in Example 3A, but using the preparation of [1S-(1α,2α,3β,5α)]-3-(phenylmethoxy)-2-[(phenylmethoxy)methyl]-6-oxabicyclo[3.1.0]hexane from step D above.

F. [1S-(1α,2β,3α,4β)]-1-[2-Hydroxy-4-(phenylmethoxy)-3-[(phenylmethoxy)methyl]cyclopentyl]-5-iodo-2,4(1H,3H)-pyrimidinedione To a solution of [1S-(1α,2β,3α,4β)]-1-[2-hydroxy-4-(phenylmethoxy)-3-[(phenylmethoxy)methyl]cyclopentyl]-2,4(1H,3H)-pyrimidinedione from step E (11.99 g., 28.41 mmol.) in dry dioxane (455 ml.) was added iodine (14.44 g., 56.85 mmol.) and 0.8N nitric acid (59.6 ml., 30.3 mmol.). The reaction was heated at 90° for 2 hours and cooled to room temperature. A saturated solution of sodium thiosulfate (25 ml.) was added until a light orange color persisted. Water (450 ml.) was added, the mixture was extracted with dichloromethane (3×500 ml.), and the combined dichloromethane extracts were washed with saturated sodium chloride solution (100 ml.), dried (sodium sulfate), and concentrated in vacuo to a residue. Chromatography of this residue over 1200 ml. of Merck silica gel using ethyl acetate-chloroform (1:1) provided 9.5 g. of desired product as a solid having m.p. 165°.

G. [1S-[1α(E),2β,3α,4β)]-3-[1,2,3,4-Tetrahydro-1-[2-hydroxy-4-(phenylmethoxy)-3-[(phenylmethoxy)methyl[cyclopentyl]-2,4-dioxo-5-pyrimidinyl]-2-propenoic acid, methyl ester A mixture of palladium (II) acetate (168 mg., 0.752 mmol.), triphenylphosphine (400 mg., 1.52 mmol.) and triethylamine (1.1 ml., 7.9 mmol.) in dioxane (100 ml., purified on basic alumina and degassed in vacuo) was heated with stirring for 15 minutes at 85° under nitrogen. To the red solution was added [1S-(1α,2β,3α,4β)]-1-[2-hydroxy-4-(phenylmethoxy)-3-[(Phenylmethoxy)methyl]cyclopentyl]-5-iodo-2,4-(1H,3H)-pyrimidinedione from step F (2.90 g., 5.28 mmol., dried in vacuo over phosphorus pentoxide at 50° for 2 hours) and methyl acrylate (1.40 ml., 15.6 mmol.). The mixture was stirred for 7 hours at 80°, 2 hours at 90°, and then at room temperature overnight. The mixture was filtered through Celite, and the Celite was washed with chloroform (200 ml.). The combined filtrates were concentrated in vacuo to a residue, which was dissolved in chloroform (200 ml.). The chloroform was washed with water, dried (sodium sulfate), and concentrated in vacuo to a residue. Chromatography of this residue on a column of Merck silica gel (600 ml., packed in dichloromethane) by eluting with a gradient of dichloromethane to 5% ethanol in dichloromethane gave 1.54 g. of desired product as a foamy solid.

H. [1S-[1α(E),2β,3α,4β)]-3-[1,2,3,4-Tetrahydro-1-[2-hydroxy-4-(phenylmethoxy)-3-[(phenylmethoxy)methyl]cyclopentyl]-2,4-dioxo-5-pyrimidinyl]-2-propenoic acid The title compound was prepared by following the procedure in Example 5B, but using the preparation of [1S-[1α(E),2β,3α,4β)]-3-[1,2,3,4-tetrahydro-1-[2-hydroxy-4-(phenylmethoxy)-3-[(phenylmethoxy)methyl]cyclopentyl]-2,4-dioxo-5-pyrimidinyl]-2-propenoic acid, methyl ester from step G above.

I. [1S-[1α(E), 2β,3α,4β]]-1-[2-Hydroxy-4-(phenylmethoxy)-3-[(phenylmethoxy)methyl]cyclopentyl]-5-(2-iodoethenyl)-2,4(1H,3H)-pyrimidinedione To a stirred solution of [1S-[1α(E),2β,3α,4β)]3-[1,2,3,4-tetrahydro-1-[2-hydroxy-4-(phenylmethoxy)-3-[(phenylmethoxy)methyl]cyclopentyl]-2,4-dioxo-5pyrimidinyl]-2-propenoic acid from step H (500 mg., 1.0 mmol., dried by concentration in vacuo from dry dimethylformamide) in 10 ml. of dry dimethylformamide under argon was added potassium acetate (1.97 g., 20.0 mmol.). The mixture was stirred at room temperature for 30 minutes, and then N-iodosuccinimide (225 mg., 1.0 mmol.) was added. The mixture was stirred at 50° for 4 hours, additional N-iodo-succinimide (113 mg., 0.5 mmol.) was added, and heating at 50° was continued for 4.5 hours. The mixture was stirred overnight at room temperature and then filtered. The solids were washed with dimethylformamide (20 ml.), and the combined filtrates were concentrated in vacuo to a residue. The residue was taken up in chloroform (125 ml.), and the chloroform solution was washed with 1M potassium bicarbonate (3×20 mi.) and water (25 ml.), dried (sodium sulfate), and concentrated in vacuo to a residue. Chromatography of the residue on a column of Merck silica gel (75 ml., packed in dichloromethane) by eluting with a gradient of dichloromethane to 3% methanol in dichloromethane gave 350 mg. of desired product as a foamy solid.

J. [1S-[1α(E),3α,4β]]-5-(2-Iodoethenyl)-1-[2-oxo-4-(phenylmethoxy)-3-[(phenylmethoxy)methyl]cyclopentyl]-2,4(1H,3H)-pyrimidinedione 1,3-Dicyclohexylcarbodiimide (868 mg., 4.2 mmol.) and methylphosphonic acid (67.2 mg., 0.7 mmol.) were added to a solution of [1S-[1α(E),2β,3α,4β]]-1-[2-hydroxy-4-(phenylmethoxy)-3-[(phenylmethoxy)methyl]cyclopentyl]-5-(2-iodoethenyl)-2,4(1H,3H)-pyrimidinedione (805 mg., 1.4 mmol., dried by concentration in vacuo from dry toluene) in dry dimethyl sulfoxide (5.6 ml.), and the mixture was stirred at room temperature under nitrogen for 6 hours. A solution of oxalic acid dihydrate (16.8 mg.) in methanol (2.2 ml.) was added, and stirring was continued for 2 hours. The reaction was filtered, the precipitate was washed with dichloromethane (30 ml.), and the combined filtrate was washed with water (4×25 ml.), dried (sodium sulfate), and concentrated in vacuo to give 930 mg. of crude desired product as a foamy residue.

K. [1S-[1α(E),3α,4β]]-5-(2-Iodoethenyl)-1-[2-methylene-4-(phenylmethoxy)-3-[(phenylmethoxy)methyl]cyclopentyl]-2,4(1H,3H)-pyrimidinedione To a solution of the crude preparation of [1S-[1α(E),-3α,4β]]-5-(2-iodoethenyl)-1-[2-oxo-4-(phenylmethoxy)-3-[(phenylmethoxy)methyl]-cyclopentyl]2,4(1H,3H)-pyrimidinedione from step J above (930 mg., dried by concentration in vacuo from dry doluene) in dry dichloromethane (17 ml.) was added a slurry of 0.3M zinc-titanium tetrachloride-dibromomethane complex in tetrahydrofuran (Preparation 2, Example 4C) (14 ml., 4.2 mmol.). The reaction was stirred at room temperature under nitrogen for 5 hours and poured into a mixture of saturated sodium bicarbonate (112 ml.) and dichloromethane (112 ml.). After stirring for 35 minutes, the mixture was filtered through Celite. The layers in the filtrate were separated, and the organic layer was washed with water (2×50 ml.), dried (sodium sulfate), and concentrated in vacuo to a residue. Chromatography of the residue on a column of Merck silica gel (100 ml., packed in chloroform) using a gradient of chloroform to 15% ethyl acetate in chloroform afforded 400 mg. of a solid consisting of 299 mg. of desired product and 101 mg. of 1,3dicyclohexylurea.

L. [1S-[1α(E),3α,4β]]-1-[4-Hydroxy-3-(hydroxymethoxyl)-2-methylenecyclopentyl]-5-(2-iodoethenyl)-2,4(1H,3H)-pyrimidinedione To a solution of 400 mg. of the preparation from step K, containing 299 mg. (0.525 mmol.) of [1S-[1α(E),-3α,4β]]-5-(2-iodoethenyl)-1-[2-methylene-4-(phenylmethoxy)-3-[(phenylmethoxy)methyl]cyclopentyl]-2,4(1H,3H)-pyrimidinedione (dried by concentration in vacuo from dry toluene), in 7.5 ml. of dry dichloromethane at −78° under nitrogen was added 1M boron trichloride in dichloromethane (5.76 ml., 5.76 mmol.). The mixture was stirred at −78° for 1 hour, and then methanol (9 ml.) was slowly added. After warming the solution to room temperature over 30 minutes, the solvents were removed in vacuo leaving a residue, which was concentrated in vacuo from toluene (3×10 ml.). The residue was taken up in methanol (24 ml.) and water (18 ml.), and the pH was adjusted to 7 using 1.0N potassium hydroxide. After concentration in vacuo to remove methanol, the aqueous suspension (15 ml.) was applied to a column of CHP 20P resin (48 ml., packed in water). Elution of the column with a gradient of water to 40% methanol in water and concentration of appropriate fractions in vacuo gave 99 mg. of desired product as a sticky solid. This solid and 10 mg. of sticky desired product from a similar reaction were combined and dissolved in 60% methanol in water. Concentration of this solution to approximately 8 ml. gave a solid, which was collected and dried in vacuo providing 89 mg. of desired product having m.p. 180°–185° dec. and $[\alpha]_D^{22}+75.7°$ (c, 0.3, methanol).

Anal. calc'd. for $C_{13}H_{15}IN_2O_4$: C, 40.02; H, 3.87; N. 7.18 Found: C, 39.81; H, 3.61; N, 7.01.

EXAMPLE 8

1S-[1α(E),3α,4β)]-5-(2-Chloroethenyl)-1-[4-hydroxy-3-(hydroxymethyl)-2-methylenecyclopentyl]-2,4(1H,3H)-pyrimidinedione A. [1S-[1α(E),2β,3α,4β]]-5-(2-Chloroethenyl)-1-[2-hydroxy-4-(phenylmethoxy)-3-[(phenylmethoxy)methyl]cyclopentyl[-2,4(1H,3H)-pyrimidinedione Potassium bicarbonate (1.55 g., 15.5 mmol.) and N-chlorosuccinimide (760 mg., 5.69 mmol.) were added to a solution of [1S-[1α(E),2β,3α,4β]]-3-[1,2,3,4-tetrahydro-1-[2-hydroxy-4-(phenylmethoxy)-3[(phenylmethoxy)methyl]cyclopentyl]-2,4-dioxo-5pyrimidinyl]-2-propenoic acid (prepared as described in Example 7H, 2.54 g., 5.17 mmol., dried by concentration in vacuo from dry dimethylformamide) in dry dimethylformamide (52 ml.), and the mixture was stirred at room temperature under nitrogen for 17 hours. The mixture was cooled to room temperature and filtered, and the filtrate was concentrated in vacuo to a residue. The residue was dissolved in ethyl acetate (750 ml.) and water (250 ml.), and the pH was adjusted to 2 using 0.1N hydrochloric acid. The ethyl acetate layer was washed with water, dried (sodium sulfate), and concentrated in vacuo to a residue. Chromatography of this residue on a column of Merck silica gel (150 ml., packed in dichloromethane) by elution with a gradient of dichloromethane to 3% ethanol in dichloromethane afforded 596 mg. of desired product as a foamy solid.

B. [1S-[1α(E),3α,4β]]-5-(2-Chloroethenyl)-1-[2-oxo-4-(phenylmethoxy)-3-[(phenylmethoxy)methyl]cyclopentyl]-2,4(1H,3H)-pyrimidinedione 1,3-Dicyclohexylcarbodiimide (806 mg., 3.9 mmol) and methylphosphonic acid (62.4 mg., 0.65 mmol.) were added to a solution of [1S-[1α(E),2β,3α,4β]]-5-(2-chloroethenyl)-1-[2-hydroxy-4-(phenylmethoxy)-3-[(phenylmethoxy)methyl]cyclopentyl]-2,4(1H,3H)-pyrimidinedione (631 mg., 1.3 mmol., dried by concentration in vacuo from dry toluene) in dry dimethyl sulfoxide (5.2 ml.), and the mixture was stirred at room temperature under nitrogen for 5 hours. A solution of oxalic acid dihydrate (15.6 mg.) in methanol (2.1 ml.) was added, and stirring was continued for 3 hours. The reaction was filtered, and the precipitate was washed with dichloromethane (3×130 ml.). The combined filtrate and washes were washed with water (4×40 ml.), dried (sodium sulfate), and concentrated in vacuo to give 850 mg., of crude desired product as a foamy residue.

C. [1S-[1α(E),3α,4β]]-5-(2-Chloroethenyl)-1-[2-methylene-4-(phenylmethoxy)-3-[(phenylmethoxy)methyl]cyclopentyl]-2,4(1H,3H)-pyrimidinedione To a solution of the crude preparation of [1S-[1α(E),3α,4β]]-5-(2-chloroethenyl)-1-[2-oxo-4-(phenylmethoxy)-3-[(phenylmethoxy)methyl]cyclopentyl]-2,4(1H,3H)-pyrimidinedione from step B above (850 mg., dried by concentration in vacuo from dry toluene) in dry dichloromethane (15.6 ml.) was added a slurry of 0.3M zinc-titanium tetrachloride-dibromomethane complex in tetrahydrofuran (Preparation 2, Example 4C) (13 ml., 3.9 mmol.). The reaction was stirred at room temperature under nitrogen for 5 hours and poured into a mixture of saturated sodium bicarbonate (145 ml.) and dichloromethane (145 ml.). After stirring for 80 minutes, the mixture was filtered through Celite. The layers in the filtrate were separated, the organic layer was washed with water (2×250 ml.), dried (sodium sulfate), and concentrated in vacuo to a residue. Chromatography of the residue on a column of Merck silica gel (110 ml., packed in chloroform) by eluting with a gradient of chloroform to 4% ethanol in chloroform afforded 554 mg. of a solid consisting mostly of desired product (approximately 310 mg.) and 1,3-dicyclohexylurea.

D. [1S-[1α(E),3α,4β]]-5-(2-Chloroethenyl)-1-[4-hydroxy-3-(hydroxymethyl)-2-methylenecyclopentyl]-2,4(1H,3H)-pyrimidinedione To a solution of 554 mg. of the preparation of step C above containing approximately 310 mg. (0.65 mmol.) of [1S-[1α(E),3α,4β]]-5-(2-chloroethenyl)-1-[2-methylene-4-(phenylmethoxy)-3-[(phenylmethoxy)methyl]cyclopentyl]-2,4(1H,3H)-pyrimidinedione (dried by concentration in vacuo from dry toluene) in 10 ml. of dry dichloromethane at −78° under nitrogen was added 1M boron trichloride in dichloromethane (7.2 ml., 7.2 mmol.). The mixture was stirred at −78° for 1 hour, and then methanol (5.5 ml.) was slowly added. After warming the solution to room temperature over 30 minutes, the solvents were removed in vacuo leaving a residue, which was concentrated in vacuo from methanol (4×5.5 ml.) and then toluene (2×8 ml.). The residue was taken up in methanol (26 ml.) and water (20 ml.), and the pH was adjusted to 7.2 using 1N potassium hydroxide. The solution was concentrated in vacuo to a suspension (15 ml.), which was applied to a column of CHP 20P resin (48 ml., packed in water). Elution of the column with a gradient of water to 60% methanol in water and concentration of appropriate combined fractions to approximately 10 ml. gave a solid, which was collected and dried in vacuo to afford 65 mg. of desired product as a white solid having m.p. 221°–223° (dec.) and $[\alpha]_D^{22}+80.7°$ (c 0.3 methanol).

Anal. calc'd. for $C_{13}H_{15}ClN_2O_4$: C, 52.27; H, 5.06; N, 9.38 Found: C, 52.03; H, 4.87; N, 9.28.

EXAMPLE 9

Treatment of Viral Infection in Cell Culture in Vitro

Assays were performed in cell culture systems to determine the concentrations of compounds that are effective in preventing several kinds of viral infections. The assays are described below, and the results are presented in Table 1.

Abbreviations:

HSV-1 (herpes simplex virus type 1, strain Schooler), HSV-2 (herpes simplex virus type 2, strain 186), VZV (varicella zoster virus, strain ELLEN), HCMV (human cytomegalovirus, strain AD 169 HIV (human immununodeficiency virus, strain HTLV-IIIB).

Cell Culture Assays:

HSV-1, HSV-2, HCMV and VZV antiviral assays: Virus was adsorbed to WI-38 cell culture monolayers in 6 well culture plates (Costar, Cambridge, Mass.) for 1 hour prior to addition of maintenance medium containing duplicate dilutions of the test compound. Inhibition of plaque development was evaluated on fixed and stained monolayers after 4 days incubation at 37° C. for HSV-1 and HSV-2, and after 5-7 days incubation at 37° C. for HCMV and VZV. $ID_{50}$ values were determined from the drug concentration which conferred at least a 50% plaque reduction compared to virus controls.

HIV antiviral assay: Suspensions of MT-2 cells (S. Harada, et al., *Science*, 229, 563 (1985)) were infected at a multiplicity of infection of 0.03 $TLID_{50}$/cell with HIV (strain HTLV-III B). After adsorption for 1-2 hours at 37° C., infected cells were diluted in growth medium (RPMI 1640 containing the antibiotics penicillin plus streptomycin and 10% fetal calf serum) to give a final cell concentration of $1 \times 10^4$ viable cells/culture well in the presence of serial dilutions of the test compound, starting at 100 μg/ml. Triplicate samples at each drug concentration were used. Cultures of uninfected MT-2 cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% $CO_2$. Following incubation, viable cell numbers were counted in each well using a colorimetric assay following incubation of cells with XTT-PMS solution (XTT tetrazolium reagent plus phenazine methosulfate PMS).

Percent reduction of viral cytopathic effect (CPE) in drug treated compared to untreated virus infected cells, and percent reduction of cell viability in drug treated uninfected cells compared to untreated controls were calculated and plotted versus the drug concentrations tested. From these plots, the $ID_{50}$ (the minimum drug concentration that inhibits CPE by 50%) for each drug was calculated. 2',3'-Dideoxycytidine and 3'-azido-3'-deoxythymidine were used as a positive drug controls.

TABLE 1

[Structure: cyclopentane ring with exocyclic =CH$_2$, HOCH$_2$ group, OH group, and R$_1$ substituent]

| R$_1$ | ID$_{50}$ (μM) for the following viruses | | | | |
|---|---|---|---|---|---|
| | HSV-1 | HSV-2 | VZV | HCMV | HIV |
| [imidazole-carboxamidine structure] | 3.6 | 7.2–18 | 18–36 | 90 | * |
| [adenine-like structure] | 191–383 | 191–383 | >96 | >38 | ** |
| [cytosine structure] | 4.2–8.4 | 2.1–4.2 | 4.2–42 | 2.1–4.2 | NA |

TABLE 1-continued

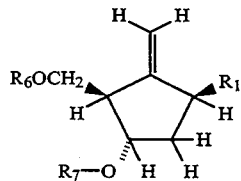

| $R_1$ | ID$_{50}$ ($\mu$M) for the following viruses | | | | |
|---|---|---|---|---|---|
| | HSV-1 | HSV-2 | VZV | HCMV | HIV |
| (5-methyl uracil) | 8–20 | 40–100 | 40–400 | ≧396 | NA |
| (5-iodo uracil) | 6–14 | >275 | 68–137 | 68–137 | NA |
| (5-(2-bromovinyl) uracil) | 0.6–1.5 | 29–73 | 0.3–0.6 | 291 | ND |
| (5-(2-iodovinyl) uracil) | 0.5–1.3 | 13–26 | 0.05–0.14 | >260 | ND |
| (5-(2-chlorovinyl) uracil) | 0.07–0.16 | 2 | 1.7 | ND | ND |

*41% reduction in viral CPE at 12 $\mu$M and 4% reduction in cell viability in uninfected cells.
**50% reduction in viral CPE at 27 $\mu$M and 23% reduction in cell viability in uninfected cells.
NA = Not Active
ND = Not determined

What we claim is:
1. A compound having the formula or a pharmaceutically acceptable salt thereof wherein:

$R_1$ is

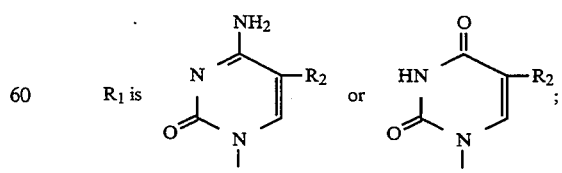

$R_2$ is fluoro, chloro, bromo, iodo, hydrogen, methyl, trifluoromethyl, ethyl, n-propyl, 2-fluoroethyl, 2-chloroethyl, ethynyl or

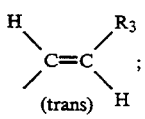

R$_3$ is chloro, bromo, iodo, hydrogen, methyl or trifluoromethyl;

R$_5$ is hydrogen, alkyl of 1 to 10 carbons, substituted alkyl of 1 to 10 carbons wherein said substituent is selected from the group consisting of halogen, amino, azido, hydroxy, cyano, trialkylammonium wherein each alkyl has 1 to 6 carbons, alkoxy of 1 to 6 carbons, phenyl, and carboxy, phenyl, or phenyl substituted with one, two or three substituents selected from the group consisting of alkyl of 1 to 6 carbons, alkoxy of 1 to 6 carbons, halogen, trifluoromethyl, amino, alkylamino of 1 to 6 carbons, dialkylamino wherein each alkyl is of 1 to 6 carbons, nitro, cyano, alkanoyloxy of 2 to 11 carbons, carboxy, carbamoyl, and hydroxy; and R$_6$ and R$_7$ are independently hydrogen, —PO$_3$H$_2$ or

2. A compound according to claim 1 wherein R$_6$ and R$_7$ are independently hydrogen or

3. A compound according to claim 1 wherein R$_6$ and R$_7$ are independently hydrogen or —PO$_3$H$_2$.

4. A compound according to claim 1 wherein R$_6$ and R$_7$ are hydrogen.

5. A compound according to claim 1 wherein R$_1$ is

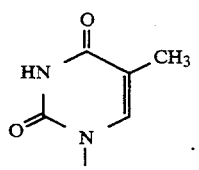

6. A compound according to claim 1 wherein R$_1$ is

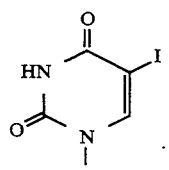

7. A compound according to claim 1 wherein R$_1$ is

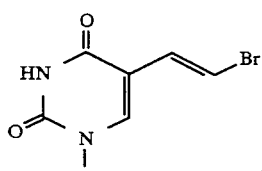

8. A compound according to claim 1 wherein R$_1$ is

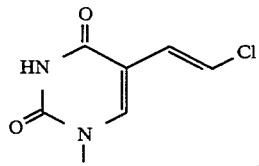

9. A compound according to claim 1 wherein R$_1$ is

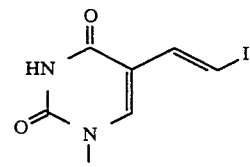

10. A compound according to claim 1 wherein R$_1$ is

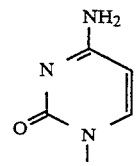

11. A compound according to claim 1, [1S-(1α,-3α,4β)]-1-[4-hydroxy-3-(hydroxymethyl)-2-methylenecyclopentyl]-5-methyl-2,4(1H,3H)-pyrimidinedione.

12. A compound according to claim 1, [1S-(1α,-3α,4β)]-4-amino-1-[4-hydroxy-3-(hydroxymethyl)-2-methylenecyclopentyl]-2(1H)-pyrimidinone.

13. A compound according to claim 1, [1S-(1α,-3α,4β)]-1-[4-hydroxy-3-(hydroxymethyl )-2-methylenecyclopentyl]-5-iodo-2,4(1H,3H)-pyrimidinedione.

14. A compound according to claim 1, [1S-[1α(E),-3α,4β]]-5-(2-bromoethenyl)-1-[4-hydroxy-3-(hydroxymethyl)-2-methylenecyclopentyl]-2,4(1H,3H)-pyrimidinedione.

15. A compound according to claim 1, [1S-[1α(E),-3α,4β]]-5-(2-chloroethenyl)-1- [4-hydroxy-3-(hydroxymethyl)-2-methylenecyclopentyl]-2,4(1H,3H)-pyrimidinedione.

16. A compound according to claim 1, [1S-[1α(E),-3α,4β]]-1-[4-hydroxy-3-(hydroxymethyl)-2-methylenecyclopentyl]-5-(2-iodoethenyl)-2,4(1H,3H)-pyrmidinedione.

17. A compound according to claim 1 wherein:

R$_1$ is 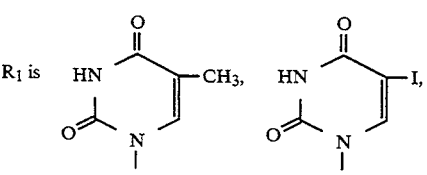

-continued

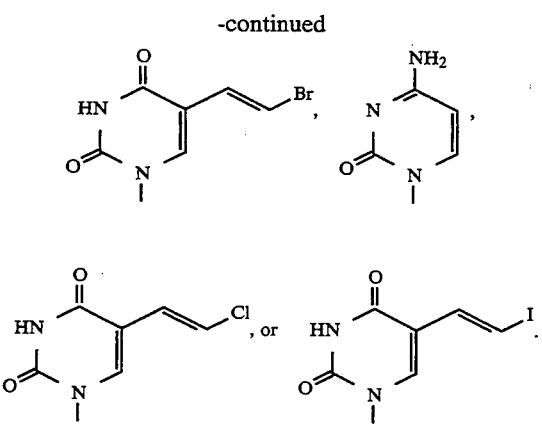

18. A compound according to claim 1 wherein:

R₁ is 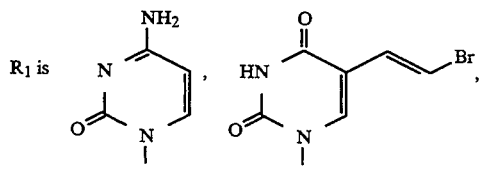

-continued

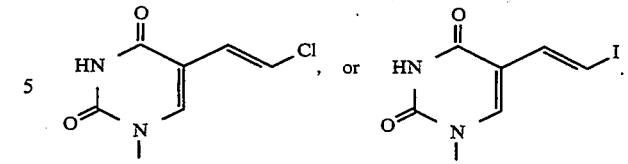

19. An antiviral composition useful for treating herpes simplex virus 1 and 2, varicella zoster virus, and human cytomegalovirus comprising a pharmaceutically acceptable carrier and an effective amount of a compound of the formula

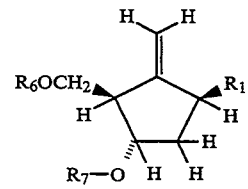

wherein $R_1$, $R_6$ and $R_7$ are as defined in claim 1.

20. A method of treating a herpes simplex virus 1, a herpes simplex virus 2, a varicella zoster virus, or a human cytomegalovirus infection in a mammalian species comprising administering an effective amount of the composition of claim 19.

* * * * *